US012761208B2

(12) United States Patent
(10) Patent No.: US 12,761,208 B2
(45) Date of Patent: Oct. 13, 2026

Rajesh et al.

(54) IPSC-DERIVED ASTROCYTES AND METHODS OF USE THEREOF

(71) Applicants: FUJIFILM Cellular Dynamics, Inc., Madison, WI (US); FUJIFILM Holdings America Corporation, Valhalla, NY (US)

(72) Inventors: Deepika Rajesh, Madison, WI (US); Christie Savic, Madison, WI (US); Sarah Burton, Madison, WI (US); Ali Fathi, Madison, WI (US); Rachel Lewis, Madison, WI (US); Robert Bradley, Madison, WI (US); Jing Liu, Madison, WI (US)

(73) Assignees: FUJIFILM Cellular Dynamics, Inc., Madison, WI (US); FUJIFILM Holdings America Corporation, Valhalla, NY (US)

( * ) Notice: Subject to any disclaimer, the term of this patent is extended or adjusted under 35 U.S.C. 154(b) by 479 days.

(21) Appl. No.: 18/344,703

(22) Filed: Jun. 29, 2023

(65) Prior Publication Data

US 2024/0003871 A1 Jan. 4, 2024

Related U.S. Application Data

(60) Provisional application No. 63/356,787, filed on Jun. 29, 2022.

(51) Int. Cl.

*G01N 33/50* (2006.01)
*C12N 5/079* (2010.01)

(52) U.S. Cl.

CPC ....... *G01N 33/5058* (2013.01); *C12N 5/0622* (2013.01); *C12N 2500/90* (2013.01);

(Continued)

(58) Field of Classification Search

None

See application file for complete search history.

(56) References Cited

U.S. PATENT DOCUMENTS 9,487,752 B2 11/2016 Meyer et al.
2006/0040392 A1* 2/2006 Collins ................ C12N 5/0607 435/372

(Continued)

FOREIGN PATENT DOCUMENTS

WO WO 2018-067826 4/2018
WO WO 2018-160496 9/2018

(Continued)

OTHER PUBLICATIONS

Liu, YIng; et al; "CD44 expression identifies astrocyte-restricted precursor cells" (Developmental Biology, 276, 31-46, 2004 (Year: 2004).*

(Continued)

*Primary Examiner* — David W Berke-Schlessel
(74) *Attorney, Agent, or Firm* — pH IP Law

(57) ABSTRACT

The present disclosure provides method for producing neural precursor cells with a glial bias from induced pluripotent cells and further differentiating the neural precursor cells to astrocytes. Further provided herein are methods for the use of the astrocytes for screening assays, models mimicking the human brain, and cell therapy.

21 Claims, 27 Drawing Sheets

(52) U.S. Cl.
CPC ...... *C12N 2501/11* (2013.01); *C12N 2501/13* (2013.01); *C12N 2501/2301* (2013.01); *C12N 2501/235* (2013.01); *C12N 2501/25* (2013.01); *C12N 2501/727* (2013.01); *C12N 2506/45* (2013.01); *C12N 2513/00* (2013.01); *C12N 2533/90* (2013.01)

(56) References Cited

U.S. PATENT DOCUMENTS

| | | | |
|---|---|---|---|
| 2009/0004661 A1 | 1/2009 | Shetty et al. |
| 2009/0311735 A1 | 12/2009 | Crook et al. |
| 2017/0253856 A1 | 9/2017 | Douvaras et al. |
| 2017/0369904 A1 | 12/2017 | Lim et al. |
| 2018/0179496 A1 | 6/2018 | Rajesh et al. |
| 2018/0305664 A1 | 10/2018 | Vodyanyk et al. |
| 2020/0263139 A1 | 8/2020 | Vodyanyk et al. |
| 2022/0041992 A1 | 2/2022 | Patel |

FOREIGN PATENT DOCUMENTS

| | | |
|---|---|---|
| WO | WO 2020-252477 | 12/2020 |
| WO | WO 2021-032271 | 2/2021 |
| WO | WO 2021-168171 | 8/2021 |

OTHER PUBLICATIONS

"Corning® Cell Culture Surfaces. The right surface for every cell," Corning Incorporated, 2014.

Appelt-Menzel et al., "Establishment of a human blood-brain barrier co-culture model mimicking the neurovascular unit using induced pluri- and multipotent stem cells," *Stem Cell Reports*, 8(4):894-906, 2017.

Atagi et al., "Apolipoprotein E Is a Ligand for Triggering Receptor Expressed on Myeloid Cells 2 (TREM2)," J Biol Chem. 290(43):26043-26050, 2015.

Breunig et al., "Neural stem cells: historical perspective and future prospects," *Neuron*, 70:614, 2011.

Caldeira et al., "Key Aging-Associated Alterations in Primary Microglia Response to Beta-Amyloid Stimulation," Front Aging Neurosci. 9:277, 2017.

Fu et al., "Cardiomyocyte differentiation of mouse iPSCs regulated by polypeptide multilayer films," *The FASEB Journal*, 28(S1), Abstract, 2014.

Gitlin et al., "Why are proteins charged? Networks of charge-charge interactions in proteins measured by charge ladders and capillary electrophoresis," *Angew. Chem. Int. Ed.*, 45-3022-3060, 2006.

Khazaei et al., "Generation of oligodendrogenic spinal neural progenitor cells from human induced pluripotent stem cells," *Current Protocols in Stem Cell Biology*, 42:2D.20.1-2D.20.14, 2017.

Melief et al., "Phenotyping primary human microglia: tight regulation of LPS responsiveness," Glia. 60(10):1506-17, 2012.

Minett et al., "Microglial immunophenotype in dementia with Alzheimer's pathology," J Neuroinflammation. 13(1):135, 2016.

PCT International Preliminary Report on Patentability issued in International Application No. PCT/US2020/037790, mailed Dec. 23, 2021.

PCT International Search Report and Written Opinion issued in International Application No. PCT/US2020/037790, mailed Dec. 3, 2020.

PCT International Search Report and Written Opinion issued in International Application No. PCT/US2023/069377, mailed Oct. 17, 2023.

Rustenhoven et al., "Brain Pericytes as Mediators of Neuroinflammation," Trends in Pharmacological Sciences, 38(3):291-304, 2017.

Shetty et al., "Clinical grade mesenchymal stem cells transdifferentiated under xenofree conditions alleviates motor deficiencies in a rat model of Parkinson's disease," *Cell Biology International*, 33(8):830-838, 2009.

Shi et al., "Directed differentiation of human pluripotent stem cells to cerebral cortex neurons and neural networks," Nature Protocols, 7(10):1836-1846, 2012.

Shi et al., "Human cerebral cortex development from pluripotent stem cells to functional excitatory synapses," Nat Neurosci 15, 477-486 (2012).

Wolfe et al., "The Role of APOE and TREM2 in Alzheimer's Disease-Current Understanding and Perspectives," Int J Mol Sci. 20(1):81, 2018.

Zheng et al., "Differentiation of glial cells from hiPSCs: potential applications in neurological diseases and cell replacement theory," *Fronteirs in Cellular Neuroscience*, vol. 12, 2018.

* cited by examiner

C

| Media 2 | Media 3 | Media 4 | Media 10 | Media 12 | Media 14 | Media 16 | Media 18 | Media 24 | Media 26 | Media 29 |
|---|---|---|---|---|---|---|---|---|---|---|
| Basal M | Basal M | Basal M | Basal M | Basal M | Basal M | Basal M | Basal M | Basal M | Basal M | Basal M |
| | | | | | | | DLL1 | DLL1 | DLL1 | DLL1 |
| | | | JAGG1 | JAGG1 | JAGG1 | JAGG1 | | | JAGG1 | JAGG1 |
| | | | | | Lipid Conc. | Lipid Conc. | | Lipid Conc. | | Lipid Conc. |
| | CT1 | CT1 | | CT1 | | CT1 | | CT1 | | |
| EGF | | EGF | EGF | EGF | EGF | EGF | EGF | EGF | EGF | EGF |

FIG. 4C

E

| Media 3 | Media 14 | Media 16 | Media 24 | Media 29 |
|---|---|---|---|---|
| Basal M | Basal M | Basal M | Basal M | Basal M |
| | | | DLL1 | DLL1 |
| | JAGG1 | JAGG1 | | JAGG1 |
| | Lipid Conc. | Lipid Conc. | Lipid Conc. | Lipid Conc. |
| CT1 | | CT1 | CT1 | |
| | EGF | EGF | EGF | EGF |

FIG. 5E

IPSC-DERIVED ASTROCYTES AND METHODS OF USE THEREOF

PRIORITY CLAIM

This application claims benefit of priority to U.S. Provisional Application Ser. No. 63/356,787, filed Jun. 29, 2022, the entire contents of which is hereby incorporated by reference.

BACKGROUND

1. Field

The present invention relates generally to the field of molecular biology and medicine. More particularly, it concerns methods of differentiating induced pluripotent stem cells to produce astrocytes.

2. Description of Related Art

Astrocytes have a central role in brain development play an important role in the central nervous system (CNS) by maintaining brain homeostasis, providing metabolic support to neurons, regulating connectivity of neural circuits, and controlling blood flow as an integral part of the blood-brain barrier. Astrocytes undergo transformation following injury or disease (e.g., reactive astrogliosis) following injury. These reactive astrocytes play a role in the onset and progression of many neurological diseases.

SUMMARY

Certain embodiments of the present disclosure provide an in vitro method for producing astrocytes from induced pluripotent stem cells (iPSCs) comprising: (a) obtaining a starting population of neural precursor cells (NPCs) derived from iPSCs; (b) culturing the NPCs in the presence of at least one leukemia inhibitory factor (LIF) receptor ligand for a period of time sufficient to produce astrocyte progenitor cells (APCs); and (c) further culturing the APCs in the presence of at least one LIF receptor ligand and lipid concentrate for a period of time sufficient to produce a population of astrocytes.

In some aspects, the iPSCs are cultured in serum free defined media. In certain aspects, the method is good-manufacturing practice (GMP) compliant. In some aspects, one or more of steps (a)-(c) are performed under xeno-free conditions, feeder-free conditions, and/or conditioned-media free conditions. In certain aspects, each of steps (a)-(c) are performed under xeno-free conditions, feeder-free conditions, and/or conditioned-media free conditions. In some aspects, each of steps (a)-(c) are performed under defined conditions. In some aspects, the iPSCs are human iPSCs.

In some aspects, obtaining the starting population of NPCs comprises: (a) culturing iPSCs on an extracellular matrix (ECM) protein coated surface in the presence of a ROCK inhibitor; (b) further culturing the iPSCs in the absence of a ROCK inhibitor or blebbistatin; (c) pre-conditioning the iPSCs in the presence of a GSK3 inhibitor; (d) differentiating the iPSCs to a population of NPCs. In some aspects, the ECM protein is laminin, fibronectin, vitronectin, MATRIGEL™, tenascin, entactin, thrombospondin, elastin, gelatin, and/or collagen. In certain aspects, the ECM protein is basement membrane extract (BME) purified from murine Engelbreth-Holm-Swarm tumor. In some aspects, the ECM protein is MATRIGEL™, laminin, or vitronectin. In some aspects, he extracellular matrix protein is MATRIGEL™. In particular aspects, the method does not comprise inhibition of SMAD signaling.

In particular aspects, steps (a)-(b) are performed under hypoxic conditions. In some aspects, the culturing of steps (a)-(b) is further defined as adherent 2-dimensional culture. In some aspects, step (a) is for about 24 hours. In particular aspects, step (b) is for about 48 hours. In certain aspects, the ROCK inhibitor is H1152. In some aspects, step (c) is performed under normoxic conditions. In some aspects, step (c) is performed for about 72 hours. In particular aspects, the GSK3 inhibitor is CHIR99021, BIO, or SB-216763. In specific aspects, the GSK3 inhibitor is CHIR99021.

In some aspects, step (d) comprises the formation of aggregates in the presence of a ROCK inhibitor. In certain aspects, the cell culture is a three-dimensional (3D) culture. In some aspects, step (d) comprises culture on ultra-low attachment plates, spinners, or bioreactors. In some aspects, step (d) is for about 8 days (e.g., 5, 6, 7, 8, 9, or 10 days).

In some aspects, the NPCs express CD24, CD184, and CD271. In some aspects, the method further comprises detecting expression of CD56, CD15, Sox1, Nestin, β3-Tubulin, Microglobulin, and/or Pax-6 in the population NPCs. In some aspects, the population of NPCs are at least 70% (e.g., 75%, 80%, 85%, or 90%) percent positive for CD24 and Nestin. In some aspects, the NPCs express Pax6 and Nestin. In certain aspects, the APCs have decreased expression of SSEA-4 and TRA-1-60 as compared to the iPSCs after step (b). In particular aspects, the NPCs are cryopreserved.

In some aspects, the iPSCs are derived from a healthy donor. In certain aspects, the iPSCs are derived from a donor with a disease. In some aspects, the disease is Alexander's disease or leukodystrophy. In some aspects, the iPSCs comprise a disruption in TREM2, APOE, Methyl-CpG Binding Protein 2 (MeCP2), and/or Alpha-synuclein (SCNA). In certain aspects, the astrocytes are end stage astrocytes positive for CD44, S100b, NFIX, GLAST, and/or GFAP. In some aspects, the astrocytes are positive for SSEA4 and CD44. In some aspects, at least 30% (e.g, 35%, 40%, 45%, or 50%) of the population of astrocytes is positive for SSEA4 and CD44. In certain aspects, the astrocytes have functional glutamate uptake and/or development of a neural network.

In certain aspects, the at least one LIF receptor ligand is Leukemia-Inhibitory Factor protein (LIF), Ciliary-Derived Neurotrophic Factor protein (CNTF), oncostatin-M protein (OSM), and/or cardiotrophin 1 (CT-1). In some aspects, step (b) further comprises culturing in the presence of lipid concentrate, EGF, JAGG1, and/or DLL1. In certain aspects, step (b) comprises culturing in the presence of LIF, CNTF, OSM, JAGG1, lipid concentrate, and EGF. In some aspects, step (b) comprises culturing in the presence of LIF, CNTF, OSM, DLL1, lipid concentrate, and EGF. In certain aspects, step (b) comprises culturing in the presence of LIF, CNTF, OSM, JAGG1, DLL1, lipid concentrate, and EGF. In some aspects, step (b) comprises culturing in the presence of LIF, CNTF, OSM, JAGG1, CT1, lipid concentrate, and EGF. In certain aspects, step (b) comprises culturing in the presence of LIF, CNTF, OSM, DLL1, CT1, lipid concentrate, and EGF.

In some aspects, the APCs are cultured in the presence of LIF, CNTF, oncostatin-M, and/or CT-1. In certain aspects, the APCs are cultured in the presence of LIF and CNTF. In some aspects, LIF, CNTF, oncostatin-M and/or CT-1 are present at a concentration of about 1-20 ng/mL (e.g., 1, 5, 10, 15, or 20 ng/mL). In specific aspects, LIF, CNTF, oncostatin-M and/or CT-1 are present at a concentration of about 10 ng/mL.

In some aspects, step (b) comprises culturing the NPCs on a Geltrex-coated surface. In certain aspects, step (b) is for about 2 weeks (e.g., 10 days, 11 days, 12 days, 13 days, 14 days, 15 days, 16 days, 17 days, 18 days, 19 days, or 20 days).

In certain aspects, step (c) comprises culturing the cells on a vitronectin-coated surface.

In some aspects, the lipid concentrate is a chemically defined lipid concentrate. In some aspects, the chemically defined lipid concentrate comprises saturated and unsaturated fatty acids. In particular aspects, the chemically defined lipid concentrate comprises arachidonic acid, cholesterol, DL-alpha-Tocopherol Acetate, linoleic acid, linolenic acid, myristic acid, oleic acid, palmitic acid, palmitoleic acid, and/or stearic acid.

In some aspects, step (c) is for about 4 weeks to 7 weeks (e.g., 4, 5, 6, or 7 weeks). In some aspects, the astrocytes express CD44, NFIX, and/or GFAP. In certain aspects, the astrocytes express CD56, S100B, CD44, GFAP, NFIX, and/or GLAST. In some aspects, the population of astrocytes is at least 80% (e.g., 80%, 85%, 90%, or 95%) positive for S100B, CD44, and/or NFIX. In some aspects, the population of astrocytes is at least 30% (e.g., 30%, 35%, 40%, 45%, or 50%) positive for CD56 and/or GFAP. In particular aspects, the astrocytes maintain network activity and uptake excess glutamate. In some aspects, the astrocytes secrete IL-1ra, IL-6, IL-8 (CXCL8), IL-10, CCL5 (RANTES), CCL7, CCL20, CXCL1, CXCL2 and/or CXCL5 after stimulation with IL-1α and/or TNFα.

Further provided herein is a pharmaceutical composition comprising as astrocyte cell population produced according to the present embodiments or aspects thereof and a pharmaceutically acceptable carrier. In some aspects, the astrocyte cell population is at least 30% e.g., 30%, 35%, 40%, 45%, or 50%) positive for SSEA4 and CD44. In particular aspects, the astrocyte cell population is at least 45% positive for SSEA4 and CD44.

Another embodiment provides a composition comprising an astrocyte cell population at least 70% (e.g., 70%, 75%, 80%, 85%, 90%, 95%, or 99%) positive for S100B, CD44, and/or NFIX, wherein the astrocyte cell population is differentiated from iPSCs. In some aspects, the astrocyte cell population is at least 80% positive for S100B, CD44, and/or NFIX. In certain aspects, the astrocyte cell population is at least 30% positive for SSEA and CD44. In some aspects, the astrocyte cell population is at least 45% positive for SSEA and CD44. In some aspects, the composition further comprises neurons.

A further embodiment provides a method for screening a test compound comprising introducing the test compound to an astrocyte cell population of the present embodiments or aspects thereof. In some aspects, the method further comprises measuring astrocyte viability and/or function.

Another embodiment provides the use of the composition of the present embodiments or aspects thereof as a model for neurodegenerative disease or injury.

In yet another embodiment, there is provided a co-culture comprising astrocytes and/or neural precursor cells produced by present embodiments or aspects thereof, endothelial cells, and pericytes. Also provided herein is the use of the co-culture of the present embodiments or aspects thereof to mimic human brain development or neurodegeneration.

Another embodiment provides a kit comprising astrocytes produced by the method of the present embodiments or aspects thereof. In some aspects, the kit further comprises endothelial cells and/or pericytes. Further provided herein is a model of neurodegeneration comprising the co-culture of the present embodiments or aspects thereof.

Also provided herein is a method for treating a neurodegenerative disease comprising administering an effective amount of the astrocyte cell composition of the present embodiments or aspects thereof to a subject. In some aspects, the disease is Alexander's disease or leukodystrophy.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Brief schematic of differentiation procedure for generating astrocytes from NPCs showing the amounts and length of time during which LIF receptor agonists were applied. (FIG. 3B) Phase contrast image of cells at day 60 plated on PLO/Laminin substrate (B top) and ICC staining for astrocyte markers CD44, NFIX and GFAP proteins at day 35 and day 80 post differentiation. A relatively small percentage of cells can be seen to express CD44 and GFAP at day 35 of the process while at day 80 CD44 expression appears completely uniform across the population and GFAP expression has increased dramatically across the population. (FIG. 3C) Quantification of percentage of positive cells for several astrocyte markers at day 70 using flow cytometry. The high expression of astrocyte and astrocyte progenitor markers S100B, NFIX and CD44 demonstrate the ability of this process to generate high purity astrocytes. GFAP and GLAST expression demonstrates that many of these cells express functional markers of mature astrocytes. The low expression of CD15 and SSEA4 show that pluripotent cells are no longer observed in the culture. (FIG. 3D) Theoretical cumulative yield over the differentiation process showed significant cell growth of over 10,000× which makes this protocol to be cost-efficient. (FIG. 3E) Time-course glutamate uptake efficacy. Glutamate uptake was performed after plating in a 96 well-plate for seven days on Matrigel. 20 μM glutamate was added for 60 min in the presence or absence of the glutamate transporter inhibitor DL-TBOA (TBOA). The measurement shown represents the percentage of glutamate concentration in −TBOA sample over the corresponding+TBOA sample. (FIG. 3F) Microelectrode assay (MEA) roster plots of different cultures before (baseline) and after glutamate application. 120,000 iCell GlutaNeurons were cultured alone or cocultured with 20,000 iCell Astrocytes or NPC astrocytes for 23 days in BrainPhys media. Synchronous bursting activity can be seen in all conditions demonstrating the formation of mature synaptic network. The number of action potentials observed in network bursts is higher in co-cultures containing either iCell Astrocytes or NPC astrocytes compared to the iCell GlutaNeuron monoculture showing the effect on network formation induced by the astrocyte coculture. Additional application of exogenous glutamate is sufficient to stop all synchronous bursting in the iCell GlutaNeuron monocultures but not in co-cultured samples showing the increased robustness of the culture to outside perturbations.

FIGS. 4A-4C: 31 media matrix experiments. (FIG. 4A) Fold expansion analysis of 31 medias tested to determine the potential of each to induce proliferation of NPCs over 14 days of differentiation time-course. Medias 5, 6, 7, 8, 13, 21, 22, 23, 30 and 31 show a nearly complete lack of cells at the end of day 14 and were excluded from further analysis (FIG. 4B Day 14 purity analysis on astrocyte lineage related marker expression by flow cytometry. Samples were collected at day 14 of the 31 media test except the samples showing a complete loss of cells in FIG. 4A. Samples from all medias tested show a lack of the pluripotency marker SSEA4 and nearly uniform expression of the astrocyte lineage marker NFIX. The neural progenitor marker remained largely unchanged between the samples though the co-expression of the astrocyte progenitor markers is higher in medias 10, 14, 16, 24, and 29. (FIG. 4C) Composition of 11 media which had the best performance based on expansion and purity in the 31 media comparison for further experimentation. These are medias 2, 3, 4, 10, 12, 14, 16, 18, 24, 26 and 29.

FIGS. 5A-5E: 11 and 5 media matrix experiments. (FIG. 5A) Flow cytometry analysis of the 11 medias determined to have the best combination of proliferation and astrocyte progenitor marker expression from FIG. 4 at D35 in the process. The near uniform expression of the astrocyte lineage marker NFIX (>90% of cells express NFIX in all media conditions except media 18) can be observed in all conditions as can the lack of the pluripotency marker SSEA4 (<10% SSEA4 expression in all media conditions except medias 14, 16, 24 and 29 where expression is less than 20%) and the NPC marker CD15 (expression of CD15 is less than 5% in all conditions). Certain conditions can be clearly seen to upregulate the expression of astrocyte markers CD44, S100B and GLAST (media conditions 14, 16, 24 and 29 show >75% CD44/S100B co-expressing cells and medias 14, 16 and 24 show >60% GLAST expression). These conditions use the medias 14, 16, 24 and 29 and therefore are the most effective in specifying the astrocyte lineage from NPC cells. (FIG. 5B) Cumulative fold expansion analysis of 11 media matrix over 35 day differentiation. Medias 14, 16, 24 and 29 can be seen to have significantly higher proliferation through D35 over the other media conditions with expansion over this time period greater than 25 fold. This combined with the higher expression of astrocyte markers from FIG. 5A indicate these medias as clearly the best in inducing a robust differentiation of astrocytes from NPC cells. (FIG. 5C) Immunocytochemistry of D49 cells from the 5 media matrix experiment. The astrocyte progenitor and astrocyte markers NFIX and CD44 can be seen to be increased in cells differentiated using medias 14, 16, 24 and 29 over the control media 3. The expression of the mature astrocyte marker GFAP is seen expressed robustly in conditions differentiated using medias 14, 16, 24 and 29 while little GFAP is observed in cells differentiated using media 3. (FIG. 5D) Glutamate uptake assay of D49 cells from the 5 media comparison study. Glutamate uptake is a common and accepted indicator of astrocyte function in vitro. The use of the glutamate transporter inhibitor TBOA is used as a control to confirm that any removal of glutamate from the media is due to the presence and activity of these astrocyte-specific transporters. Cells differentiated using medias 14, 16, 24 and 29 were able to demonstrate a reduction in measured glutamate in the media after 1 hour of incubation. Cells differentiated using media 3 were not able to significantly uptake glutamate. (FIG. 5E) Outline of 5 media which had the best performance in the 11 media comparison for further study.

(FIG. 6A) Representative flow cytometry plots of surface CD56/SSEA4 co-staining on D28 and intracellular CD44/SSEA4 co-staining on both D28 and D35 from media 14 condition. The emergence of cells co-expressing the astrocyte marker CD44 and SSEA4, a classical marker of pluripotent cells, is demonstrated. This combination of markers on astrocytes has not been previously demonstrated. Time course of surface SSEA4 expression and intracellular CD44 expression from D7 to D35 for (FIG. 6B) condition 3, (FIG. 6C) condition 14, (FIG. 6D) condition 16, (FIG. 6E) condition 24, and (FIG. 6F) condition 29. The emergence of a CD44 and SSEA4 co-positive population can be observed after D35 in astrocytes differentiated from media conditions 14, 16 and 24 where expression increased from below 20% by D35 but increased to over 90% by day 42. This occurrence was not observed in condition 29 or in the control cells differentiated using media 3. Media conditions 14, 16 and 24 were continued to D42. Differential expression of SSEA4 and CD44 from surface and intracellular staining on D28 and D35. Summary of expression profiles of (FIG. 6G) condition 14, (FIG. 6H) condition 16, (FIG. 6I) condition 24, and (FIG. 6J) condition 29.

(FIG. 7A) Immunocytochemistry of 7 day post-thaw astrocytes cultured in either Astro3 media, AMM or BrainPhys Complete media. All medias used post-thaw are equally capable of supporting the expression of the astrocyte marker genes GFAP, CD44 and NFIX (FIG. 7B) Glutamate uptake assay of 7 day post-thaw astrocytes cultured in either Astro3 media, AMM or BrainPhys Complete media. All medias were equally capable of supporting astrocyte function and astrocytes cultured in all medias displayed a robust glutamate uptake function. (FIG. 7C) Quantified results from the MEA data analysis. iCell GlutaNeurons were cultured alone or in co-culture with NPC astrocytes. An increase in network burst frequency can be seen in neurons co-cultured with NPC astrocytes (Gluta+C1).

(FIG. 8A) Astrocytes were capable of robust secretion of IL-1ra after stimulation with IL-1alpha, IFN-gamma, TNF-alpha or combinations thereof. Stimulation with IL-1alpha or TNF-alpha resulted in over a three-fold induction of IL-1ra secretion. TNF-alpha combined with IL-1alpha or IL-1beta resulted in an increase of approximately 14-fold over unstimulated control. The combination of IFN-gamma with TNF-alpha produced the highest fold-change over control, with over 84-fold secretion of IL-1ra compared to control. IL-1ra binds to cell surface IL-1 receptors, blocking binding of pro-inflammatory IL-1alpha and IL-1beta. (FIG. 8B) Astrocytes were capable of robust secretion of IL-6 after stimulation with IL-1alpha, TNF-alpha or combinations thereof. IFN-gamma alone or combined with TNF-alpha resulted in increased secretion of IL-6 by 32- and 39-fold, respectively, over unstimulated control. IL-alpha stimulation resulted in over 400-fold increase of IL-6 secretion compared to control. TNF-alpha combined with either IL-1alpha or IL-1beta increased IL-6 secretion by over 3300-fold compared to control. IL-6 attracts pro-inflammatory T cells and promotes demyelination. (FIG. 8C) Astrocytes were capable of robust secretion of IL-8/CXCL8 after stimulation with IL-1alpha, TNF-alpha or combinations thereof. TNF-alpha alone or combined with IFN-gamma resulted in increased secretion of IL-8 by 898- and 665-fold, respectively, over unstimulated control. IL-alpha stimulation resulted in over 3300-fold increase of IL-8 secretion compared to control. TNF-alpha combined with either IL-1alpha or IL-1beta increased IL-8 secretion by over 12,000-fold compared to control. IL-8/CXCL8 is secreted by astrocytes to attract pro-inflammatory immune cells after insults. This analyte also plays a role in recruitment and differentiation of oligodendrocyte precursor cells (OPCs) to promote remyelination. (FIG. 8D) Astrocytes were capable of robust secretion of IL-10 after stimulation with IL-1alpha, IFN-gamma, TNF-alpha or combinations thereof. IFN-gamma stimulation resulted in increased secretion of IL-10 by 161-fold over unstimulated control. IL-alpha stimulation resulted in over 415-fold increase of IL-10 secretion compared to control. TNF-alpha alone, or combined with IL-1alpha, IL-1beta or IFN-gamma increased IL-10 secretion by over 1000-fold compared to control. IL-10 is secreted by astrocytes to reduce iNos activity and reduce astrogliosis. (FIG. 8E) Astrocytes were capable of robust secretion of CCL5/RANTES after stimulation with IL-1alpha, TNF-alpha or combinations thereof. IL-1alpha stimulation resulted in increased secretion of CCL5/RANTES by 156-fold over unstimulated control. TNF-alpha alone, or combined with IL-1alpha, IL-1beta or IFN-gamma increased CCL5/RANTES secretion by over 2500-fold compared to control. CCL5/RANTES controls the movements of peripheral immune cells. (FIG. 8F) Astrocytes were capable of robust secretion of CCL7 after stimulation with IL-1alpha, TNF-alpha or combinations thereof. TNF-alpha stimulation resulted in increased CCL7 secretion of 1184-fold over control. IL-1alpha stimulation resulted in increased secretion of CCL7 by 2177-fold over unstimulated control. IFN-gamma with TNF-alpha stimulation increased CCL7 secretion by 3745-fold over unstimulated control. TNF-alpha combined with IL-1alpha or IL-1beta increased CCL7 secretion by over 15,000-fold compared to control. CCL7 is important for astrocyte-microglia interactions and induces microglia activation. (G) Astrocytes were capable of robust secretion of CCL20 after stimulation with IL-1alpha, TNF-alpha or combinations thereof. Stimulation with IL-1alpha or TNF-alpha alone increased CCL20 secretion by over 18-fold over unstimulated control. TNF-alpha combined with IL-1alpha, IL-1beta or IFN-gamma increased CCL20 secretion by over 100-fold compared to control. CCL20 is secreted by astrocytes in response to pro-inflammatory stimuli and attracts T-cells, B-cells and DCs. (FIG. 8H) Astrocytes were capable of robust secretion of CXCL1 after stimulation with IL-1alpha, TNF-alpha or combinations thereof. TNF-alpha alone or combined with IFN-gamma resulted in over 9-fold secretion of CXCL1 over control. Stimulation with IL-1alpha increased CXCL1 secretion by 84-fold over unstimulated control. TNF-alpha combined with IL-1alpha or IL-1beta increased CXCL1 secretion by over 450-fold compared to control. CXCL1 is secreted by astrocytes to recruit neutrophils to the site of infection, and increases BBB permeability. (FIG. 8I) Astrocytes were capable of robust secretion of CXCL2 after stimulation with IL-1alpha, TNF-alpha or combinations thereof. TNF-alpha alone or combined with IFN-gamma resulted in over 51-fold secretion of CXCL2 over control. Stimulation with IL-1alpha increased CXCL2 secretion by 379-fold over unstimulated control. TNF-alpha combined with IL-1alpha or IL-1beta increased CXCL2 secretion by over 1585-fold compared to control. CXCL2 activates CXCR2, found on oligodendrocytes and OPCs, which increases OPC proliferation and differentiation. (FIG. 8J) Astrocytes were capable of robust secretion of CXCL5 after stimulation with IL-1alpha, TNF-alpha or combinations thereof. TNF-alpha alone or combined with IFN-gamma resulted in over 47-fold secretion of CXCL5 over control. Stimulation with IL-1alpha increased CXCL5 secretion by 161-fold over unstimulated control. TNF-alpha combined with IL-1alpha or IL-1beta increased CXCL5 secretion by over 872-fold compared to control. CXCL5 is secreted by astrocytes in response to injury and activates microglia, resulting in decreased microglia phagocytosis and inhibition.

DESCRIPTION OF ILLUSTRATIVE EMBODIMENTS

Figure 1:
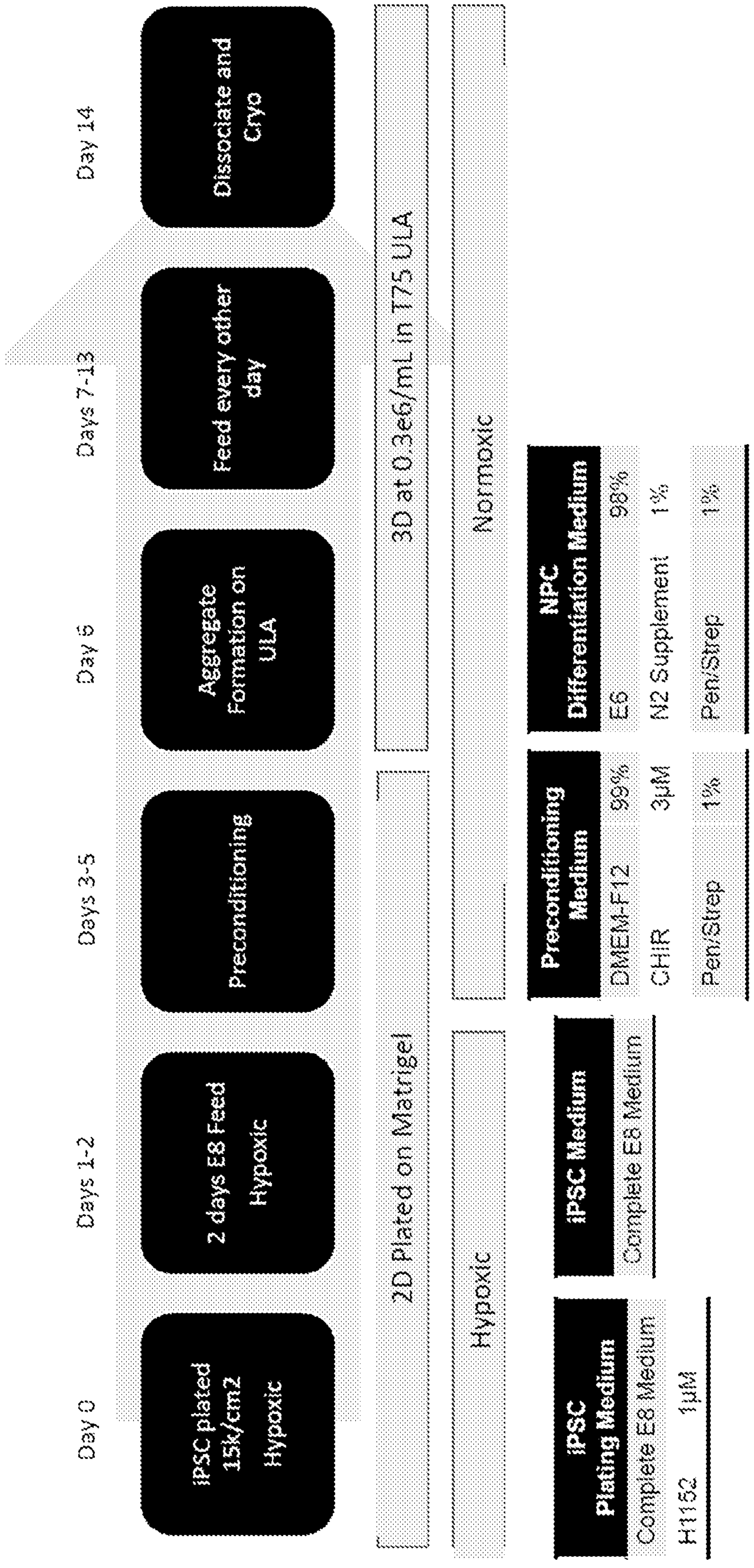
FIG. 1: Schematic depicting the method of neural progenitor cell (NPC) generation.

In certain embodiments, the present disclosure provides methods for the production of neural precursor cells (NPCs) with a glial bias, also referred to herein as iPSC-derived glial progenitors, for the production of astrocytes. In particular aspects, the method is a defined serum-free method for generating astrocytes, such as for preclinical and/or clinical applications.

In the present studies, NPCs with a glial bias were generated from multiple iPSC lines and placed in a chemically defined astrocyte differentiation media to generate end stage astrocytes efficiently. End stage astrocytes expressed the key astrocyte markers such as CD44, NFIX and GFAP and demonstrated glutamate uptake and facilitated the development of a neuronal network. In process marker analysis identified the reemergence of SSEA4, (a pluripotent stem cell marker), co-expressed along with the astrocyte progenitor marker CD44. The present studies further showed that end stage astrocytes can be successfully cryopreserved and used in multiple cell assay specific applications, pre-clinical application or clinical applications either pre- or post-cryoprservation. Further embodiments provide methods for identifying agents which modulate astrocyte viability or function as well as a triculture kit for mimicking neurodegeneration. The astrocytes generated by the present methods can also be used for cell therapy applications, including therapeutic applications to treat neurologic and brain related diseases or conditions. The astrocytes produced by the present methods may be used for disease modeling, drug discovery, and/or regenerative medicine.

I. Definitions

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "essentially" is to be understood that methods or compositions include only the specified steps or materials and those that do not materially affect the basic and novel characteristics of those methods and compositions.

As used herein, a composition or media that is "substantially free" of a specified substance or material contains ≤30%, ≤20%, ≤15%, more preferably ≤10%, even more preferably ≤5%, or most preferably ≤1% of the substance or material.

The terms "substantially" or "approximately" as used herein may be applied to modify any quantitative comparison, value, measurement, or other representation that could permissibly vary without resulting in a change in the basic function to which it is related.

The term "about" means, in general, within a standard deviation of the stated value as determined using a standard analytical technique for measuring the stated value. The terms can also be used by referring to plus or minus 5% of the stated value.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

"Feeder-free" or "feeder-independent" is used herein to refer to a culture supplemented with cytokines and growth factors (e.g., TGFβ, bFGF, LIF) as a replacement for the feeder cell layer. Thus, "feeder-free" or feeder-independent culture systems and media may be used to culture and maintain pluripotent cells in an undifferentiated and proliferative state. In some cases, feeder-free cultures utilize an animal-based matrix (e.g. MATRIGEL™) or are grown on a substrate such as fibronectin, collagen, or vitronectin. These approaches allow human stem cells to remain in an essentially undifferentiated state without the need for mouse fibroblast "feeder layers."

"Feeder layers" are defined herein as a coating layer of cells such as on the bottom of a culture dish. The feeder cells can release nutrients into the culture medium and provide a surface to which other cells, such as pluripotent stem cells, can attach.

The term "defined" or "fully-defined," when used in relation to a medium, an extracellular matrix, or a culture condition, refers to a medium, an extracellular matrix, or a culture condition in which the chemical composition and amounts of approximately all the components are known. For example, a defined medium does not contain undefined factors such as in fetal bovine serum, bovine serum albumin or human serum albumin. Generally, a defined medium comprises a basal media (e.g., Dulbecco's Modified Eagle's Medium (DMEM), F12, or Roswell Park Memorial Institute Medium (RPMI) 1640, containing amino acids, vitamins, inorganic salts, buffers, antioxidants, and energy sources) which is supplemented with recombinant albumin, chemically defined lipids, and recombinant insulin. An example of a fully defined medium is Essential 8™ medium.

For a medium, extracellular matrix, or culture system used with human cells, the term "Xeno-Free (XF)" refers to a condition in which the materials used are not of non-human animal-origin.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Prophylactically treating" includes: (1) reducing or mitigating the risk of developing the disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that amount of the compound which, when administered to a subject or patient for treating or preventing a disease, is an amount sufficient to affect such treatment or prevention of the disease.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Induced pluripotent stem cells (iPSCs)" are cells generated by reprogramming a somatic cell by expressing or inducing expression of a combination of factors (herein referred to as reprogramming factors). iPSCs can be generated using fetal, postnatal, newborn, juvenile, or adult somatic cells. In certain embodiments, factors that can be used to reprogram somatic cells to pluripotent stem cells include, for example, Oct4 (sometimes referred to as Oct 3/4), Sox2, c-Myc, Klf4, Nanog, and Lin28. In some embodiments, somatic cells are reprogrammed by expressing at least two reprogramming factors, at least three reprogramming factors, or four reprogramming factors to reprogram a somatic cell to a pluripotent stem cell.

The term "extracellular matrix protein" refers to a molecule which provides structural and biochemical support to the surrounding cells. The extracellular matrix protein can be recombinant and also refers to fragments or peptides thereof. Examples include collagen and heparin sulfate.

A "three-dimensional (3-D) culture" refers to an artificially-created environment in which biological cells are permitted to grow or interact with their surroundings in all three dimensions. The 3-D culture can be grown in various cell culture containers such as bioreactors, small capsules in which cells can grow into spheroids, or non-adherent culture plates. In particular aspects, the 3-D culture is scaffold-free. In contrast, a "two-dimensional (2-D)" culture refers to a cell culture such as a monolayer on an adherent surface.

As used herein, a "disruption" of a gene refers to the elimination or reduction of expression of one or more gene products encoded by the subject gene in a cell, compared to the level of expression of the gene product in the absence of the disruption. Exemplary gene products include mRNA and protein products encoded by the gene. Disruption in some cases is transient or reversible and in other cases is permanent. Disruption in some cases is of a functional or full-length protein or mRNA, despite the fact that a truncated or non-functional product may be produced. In some embodiments herein, gene activity or function, as opposed to expression, is disrupted. Gene disruption is generally induced by artificial methods, i.e., by addition or introduction of a compound, molecule, complex, or composition, and/or by disruption of nucleic acid of or associated with the gene, such as at the DNA level. Exemplary methods for gene disruption include gene silencing, knockdown, knockout, and/or gene disruption techniques, such as gene editing. Examples include antisense technology, such as RNAi, siRNA, shRNA, and/or ribozymes, which generally result in transient reduction of expression, as well as gene editing techniques which result in targeted gene inactivation or disruption, e.g., by induction of breaks and/or homologous recombination. Examples include insertions, mutations, and deletions. The disruptions typically result in the repression and/or complete absence of expression of a normal or "wild type" product encoded by the gene. Exemplary of such gene disruptions are insertions, frameshift and missense mutations, deletions, knock-in, and knock-out of the gene or part of the gene, including deletions of the entire gene. Such disruptions can occur in the coding region, e.g., in one or more exons, resulting in the inability to produce a full-length product, functional product, or any product, such as by insertion of a stop codon. Such disruptions may also occur by disruptions in the promoter or enhancer or other region affecting activation of transcription, so as to prevent transcription of the gene. Gene disruptions include gene targeting, including targeted gene inactivation by homologous recombination.

II. Induced Pluripotent Stem Cells

In some embodiments, the present methods concern differentiating iPSCs. The induction of pluripotency was originally achieved in 2006 using mouse cells (Yamanaka et al. 2006) and in 2007 using human cells (Yu et al. 2007; Takahashi et al. 2007) by reprogramming of somatic cells via the introduction of transcription factors that are linked to pluripotency. Pluripotent stem cells can be maintained in an undifferentiated state and can differentiate into any adult cell type.

With the exception of germ cells, any somatic cell can be used as a starting point for iPSCs. For example, cell types could be keratinocytes, fibroblasts, hematopoietic cells, mesenchymal cells, liver cells, or stomach cells. T cells may also be used as a source of somatic cells for reprogramming (U.S. Pat. No. 8,741,648). There is no limitation on the degree of cell differentiation or the age of an animal from which cells are collected; even undifferentiated progenitor cells (including somatic stem cells) and finally differentiated mature cells can be used as sources of somatic cells in the methods disclosed herein. iPSCs can be grown under conditions that are known to differentiate human ES cells into specific cell types, and express human ES cell markers including: SSEA-1, SSEA-3, SSEA-4, TRA-1-60, and TRA-1-81.

A. HLA Matching

Major Histocompatibility Complex (MHC) is the main cause of immune-rejection of allogeneic organ transplants. There are three major class I MHC haplotypes (A, B, and C) and three major MHC class II haplotypes (DR, DP, and DQ).

MHC compatibility between a donor and a recipient increases significantly if the donor cells are HLA homozygous, i.e. contain identical alleles for each antigen-presenting protein. Most individuals are heterozygous for MHC class I and II genes, but certain individuals are homozygous for these genes. These homozygous individuals can serve as super donors, and grafts generated from their cells can be transplanted in all individuals that are either homozygous or heterozygous for that haplotype. Furthermore, if homozygous donor cells have a haplotype found in high frequency in a population, these cells may have application in transplantation therapies for a large number of individuals.

Accordingly, the iPSCs can be produced from somatic cells of the subject to be treated, or another subject with the same or substantially the same HLA type as that of the patient. In one case, the major HLAs (e.g., the three major loci of HLA-A, HLA-B and HLA-DR) of the donor are identical to the major HLAs of the recipient. In some cases, the somatic cell donor may be a super donor; thus, iPSCs derived from a MHC homozygous super donor may be used to generate differentiated cells. Thus, the iPSCs derived from a super donor may be transplanted in subjects that are either homozygous or heterozygous for that haplotype. For example, the iPSCs can be homozygous at two HLA alleles such as HLA-A and HLA-B. As such, iPSCs produced from super donors can be used in the methods disclosed herein, to produce differentiated cells that can potentially "match" a large number of potential recipients.

B. Reprogramming Factors

Somatic cells can be reprogrammed to produce induced pluripotent stem cells (iPSCs) using methods known to one of skill in the art. One of skill in the art can readily produce induced pluripotent stem cells; see for example, Published U.S. Patent Application No. 20090246875, Published U.S. Patent Application No. 2010/0210014; Published U.S. Patent Application No. 20120276636; U.S. Pat. Nos. 8,058,065; 8,129,187; 8,278,620; PCT Publication NO. WO 2007/069666 A1, and U.S. Pat. No. 8,268,620, which are incorporated herein by reference. Generally, nuclear reprogramming factors are used to produce pluripotent stem cells from a somatic cell. In some embodiments, at least two, at least three, or at least four, of Klf4, c-Myc, Oct3/4, Sox2, Nanog, and Lin28 are utilized. In other embodiments, Oct3/4, Sox2, c-Myc and Klf4 are utilized. In some aspects, five, six, seven, or eight reprogramming factors are used.

The cells are treated with a nuclear reprogramming substance, which is generally one or more factor(s) capable of inducing an iPSC from a somatic cell or a nucleic acid that encodes these substances (including forms integrated in a vector). The nuclear reprogramming substances generally include at least Oct3/4, Klf4 and Sox2 or nucleic acids that encode these molecules. A functional inhibitor of p53, L-myc or a nucleic acid that encodes L-myc, and Lin28 or Lin28b or a nucleic acid that encodes Lin28 or Lin28b, can be utilized as additional nuclear reprogramming substances. Nanog can also be utilized for nuclear reprogramming. As disclosed in published U.S. Patent Application No. 20120196360, exemplary reprogramming factors for the production of iPSCs include (1) Oct3/4, Klf4, Sox2, L-Myc (Sox2 can be replaced with Sox1, Sox3, Sox15, Sox17 or Sox18; Klf4 is replaceable with Klf1, Klf2 or Klf5); (2) Oct3/4, Klf4, Sox2, L-Myc, TERT, SV40 Large T antigen (SV40LT); (3) Oct3/4, Klf4, Sox2, L-Myc, TERT, human papilloma virus (HPV)16 E6; (4) Oct3/4, Klf4, Sox2, L-Myc, TERT, HPV16 E7 (5) Oct3/4, Klf4, Sox2, L-Myc, TERT, HPV16 E6, HPV16 E7; (6) Oct3/4, Klf4, Sox2, L-Myc, TERT, Bmi1; (7) Oct3/4, Klf4, Sox2, L-Myc, Lin28; (8) Oct3/4, Klf4, Sox2, L-Myc, Lin28, SV40LT; (9) Oct3/4, Klf4, Sox2, L-Myc, Lin28, TERT, SV40LT; (10) Oct3/4, Klf4, Sox2, L-Myc, SV40LT; (11) Oct3/4, Esrrb, Sox2, L-Myc (Esrrb is replaceable with Esrrg); (12) Oct3/4, Klf4, Sox2; (13) Oct3/4, Klf4, Sox2, TERT, SV40LT; (14) Oct3/4, Klf4, Sox2, TERT, HP VI 6 E6; (15) Oct3/4, Klf4, Sox2, TERT, HPV16 E7; (16) Oct3/4, Klf4, Sox2, TERT, HPV16 E6, HPV16 E7; (17) Oct3/4, Klf4, Sox2, TERT, Bmi1; (18) Oct3/4, Klf4, Sox2, Lin28 (19) Oct3/4, Klf4, Sox2, Lin28, SV40LT; (20) Oct3/4, Klf4, Sox2, Lin28, TERT, SV40LT; (21) Oct3/4, Klf4, Sox2, SV40LT; or (22) Oct3/4, Esrrb, Sox2 (Esrrb is replaceable with Esrrg). In one non-limiting example, Oct3/4, Klf4, Sox2, and c-Myc are utilized. In other embodiments, Oct4, Nanog, and Sox2 are utilized; see for example, U.S. Pat. No. 7,682,828, which is incorporated herein by reference. These factors include, but are not limited to, Oct3/4, Klf4 and Sox2. In other examples, the factors include, but are not limited to Oct 3/4, Klf4 and Myc. In some non-limiting examples, Oct3/4, Klf4, c-Myc, and Sox2 are utilized. In other non-limiting examples, Oct3/4, Klf4, Sox2 and Sal 4 are utilized. Factors like Nanog, Lin28, Klf4, or c-Myc can increase reprogramming efficiency and can be expressed from several different expression vectors. For example, an integrating vector such as the EBV element-based system can be used (U.S. Pat. No. 8,546,140). In a further aspect, reprogramming proteins could be introduced directly into somatic cells by protein transduction. Reprogramming may further comprise contacting the cells with one or more signaling receptors including glycogen synthase kinase 3 (GSK-3) inhibitor, a mitogen-activated protein kinase kinase (MEK) inhibitor, a transforming growth factor beta (TGF-β) receptor inhibitor or signaling inhibitor, leukemia inhibitory factor (LIF), a p53 inhibitor, an NF-kappa B inhibitor, or a combination thereof. Those regulators may include small molecules, inhibitory nucleotides, expression cassettes, or protein factors. It is anticipated that virtually any iPS cells or cell lines may be used.

Mouse and human cDNA sequences of these nuclear reprogramming substances are available with reference to the NCBI accession numbers mentioned in WO 2007/069666, which is incorporated herein by reference. Methods for introducing one or more reprogramming substances, or nucleic acids encoding these reprogramming substances, are known in the art, and disclosed for example, in published U.S. Patent Application No. 2012/0196360 and U.S. Pat. No. 8,071,369, which both are incorporated herein by reference.

Once derived, iPSCs can be cultured in a medium sufficient to maintain pluripotency. The iPSCs may be used with various media and techniques developed to culture pluripotent stem cells, more specifically, embryonic stem cells, as described in U.S. Pat. No. 7,442,548 and U.S. Patent Pub. No. 2003/0211603. In the case of mouse cells, the culture is carried out with the addition of Leukemia Inhibitory Factor (LIF) as a differentiation suppression factor to an ordinary medium. In the case of human cells, it is desirable that basic fibroblast growth factor (bFGF) be added in place of LIF. Other methods for the culture and maintenance of iPSCs, as would be known to one of skill in the art, may be used.

In certain embodiments, undefined conditions may be used; for example, pluripotent cells may be cultured on fibroblast feeder cells or a medium that has been exposed to fibroblast feeder cells in order to maintain the stem cells in an undifferentiated state. In some embodiments, the cell is cultured in the co-presence of mouse embryonic fibroblasts treated with radiation or an antibiotic to terminate the cell division, as feeder cells. Alternately, pluripotent cells may be cultured and maintained in an essentially undifferentiated state using a defined, feeder-independent culture system, such as a TESR™ medium (Ludwig et al., 2006a; Ludwig et al., 2006b) or E8™ medium (Chen et al., 2011).

C. Plasmids

In some embodiments, the iPSC can be modified to express exogenous nucleic acids, such as to include an enhancer operably linked to a promoter and a nucleic acid sequence encoding a first marker. The construct can also include other elements, such as a ribosome binding site for translational initiation (internal ribosomal binding sequences), and a transcription/translation terminator. Generally, it is advantageous to transfect cells with the construct. Suitable vectors for stable transfection include, but are not limited to retroviral vectors, lentiviral vectors and Sendai virus.

In some embodiments plasmids that encode a marker are composed of: (1) a high copy number replication origin, (2) a selectable marker, such as, but not limited to, the neo gene for antibiotic selection with kanamycin, (3) transcription termination sequences, including the tyrosinase enhancer and (4) a multicloning site for incorporation of various nucleic acid cassettes; and (5) a nucleic acid sequence encoding a marker operably linked to the tyrosinase promoter. There are numerous plasmid vectors that are known in the art for inducing a nucleic acid encoding a protein. These include, but are not limited to, the vectors disclosed in U.S. Pat. Nos. 6,103,470; 7,598,364; 7,989,425; and 6,416,998, which are incorporated herein by reference. In some aspects, the plasmid comprises a "suicide gene" which, upon administration of a prodrug, effects transition of a gene product to a compound which kills its host cell. Examples of suicide gene/prodrug combinations which may be used are truncated EGFR and cetuximab; Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

A viral gene delivery system can be an RNA-based or DNA-based viral vector. An episomal gene delivery system can be a plasmid, an Epstein-Barr virus (EBV)-based episomal vector, a yeast-based vector, an adenovirus-based vector, a simian virus 40 (SV40)-based episomal vector, a bovine papilloma virus (BPV)-based vector, or a lentiviral vector.

Markers include, but are not limited to, fluorescence proteins (for example, green fluorescent protein or red fluorescent protein), enzymes (for example, horse radish peroxidase or alkaline phosphatase or firefly/renilla luciferase or nanoluc), or other proteins. A marker may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the marker of the cell type of interest. The markers can also be identified by a biochemical or enzyme assay or biological response that depends on the function of the gene product. Nucleic acid sequences encoding these markers can be operably linked to the tyrosinase enhancer. In addition, other genes can be included, such as genes that may influence stem cell differentiation, or cell function, or physiology, or pathology.

D. Delivery Systems

Introduction of a nucleic acid, such as DNA or RNA, into the engineered cells lines of the current disclosure may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Viral Vectors

Viral vectors may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present disclosure are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

2. Episomal Vectors

The use of plasmid- or liposome-based extra-chromosomal (i.e., episomal) vectors may be also provided in certain aspects of the present disclosure. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

In certain aspects, reprogramming factors are expressed from expression cassettes comprised in one or more exogenous episomal genetic elements (see U.S. Patent Publication 2010/0003757, incorporated herein by reference). Thus, iPSCs can be essentially free of exogenous genetic elements, such as from retroviral or lentiviral vector elements. These iPSCs are prepared by the use of extra-chromosomally replicating vectors (i.e., episomal vectors), which are vectors capable of replicating episomally to make iPSCs essentially free of exogenous vector or viral elements (see U.S. Pat. No. 8,546,140, incorporated herein by reference; Yu et al., 2009). A number of DNA viruses, such as adenoviruses, Simian vacuolating virus 40 (SV40) or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based including or Epstein-Barr Virus (EBV) as defined above may replicate extra-chromosomally and help deliver reprogramming genes to somatic cells. Useful EBV elements are OriP and EBNA-1, or their variants or functional equivalents. An additional advantage of episomal vectors is that the exogenous elements will be lost with time after being introduced into cells, leading to self-sustained iPSCs essentially free of these elements.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Also, other sources of episome-based vectors are contemplated, such as yeast ARS, adenovirus, SV40, or BPV.

One of skill in the art would be well-equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Regulatory Elements

Expression cassettes included in reprogramming vectors useful in the present disclosure preferably contain (in a 5'-to-3' direction) a eukaryotic transcriptional promoter operably linked to a protein-coding sequence, splice signals including intervening sequences, and a transcriptional termination/polyadenylation sequence.

a. Promoter/Enhancers

The expression constructs provided herein comprise promoter to drive expression of the programming genes. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the $-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007).

Tissue-specific transgene expression, especially for reporter gene expression in hematopoietic cells and precursors of hematopoietic cells derived from programming, may be desirable as a way to identify derived hematopoietic cells and precursors. To increase both specificity and activity, the use of cis-acting regulatory elements has been contemplated. For example, a hematopoietic cell-specific promoter may be used. Many such hematopoietic cell-specific promoters are known in the art.

In certain aspects, methods of the present disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

Many hematopoietic cell promoter and enhancer sequences have been identified, and may be useful in present methods. See, e.g., U.S. Pat. No. 5,556,954; U.S. Patent App. 20020055144; U.S. Patent App. 20090148425.

b. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of programming genes in the constructs provided in the present disclosure. For example, cleavage sequences could be used to co-express genes by linking open reading frames to form a single cistron. An exemplary cleavage sequence is the F2A (Foot-and-mouth diease virus 2A) or a "2A-like" sequence (e.g., *Thosea asigna* virus 2A; T2A) (Minskaia and Ryan, 2013). In particular embodiments, an F2A-cleavage peptide is used to link expression of the genes in the multi-lineage construct.

c. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively, a replication origin of other extra-chromosomally replicating virus as described above or an autonomously replicating sequence (ARS) can be employed.

d. Selection and Screenable Markers

In certain embodiments, cells containing a nucleic acid construct may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

E. Gene Disruption

In certain aspects, TREM2, APOE, MeCP2, and/or SCNA gene expression, activity or function is disrupted in cells, such as PSCs (e.g., ESCs or iPSCs). In some embodiments, the gene disruption is carried out by effecting a disruption in the gene, such as a knock-out, insertion, missense or frameshift mutation, such as biallelic frameshift mutation, deletion of all or part of the gene, e.g., one or more exon or portion therefore, and/or knock-in. For example, the disruption can be effected be sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the gene or a portion thereof.

In some embodiments, the disruption of the expression, activity, and/or function of the gene is carried out by disrupting the gene. In some aspects, the gene is disrupted so that its expression is reduced by at least at or about 20, 30, or 40%, generally at least at or about 50, 60, 70, 80, 90, or 95% as compared to the expression in the absence of the gene disruption or in the absence of the components introduced to effect the disruption.

In some embodiments, the disruption is transient or reversible, such that expression of the gene is restored at a later time. In other embodiments, the disruption is not reversible or transient, e.g., is permanent.

In some embodiments, gene disruption is carried out by induction of one or more double-stranded breaks and/or one or more single-stranded breaks in the gene, typically in a targeted manner. In some embodiments, the double-stranded or single-stranded breaks are made by a nuclease, e.g., an endonuclease, such as a gene-targeted nuclease. In some aspects, the breaks are induced in the coding region of the gene, e.g., in an exon. For example, in some embodiments, the induction occurs near the N-terminal portion of the coding region, e.g., in the first exon, in the second exon, or in a subsequent exon.

In some aspects, the double-stranded or single-stranded breaks undergo repair via a cellular repair process, such as by non-homologous end-joining (NHEJ) or homology-directed repair (HDR). In some aspects, the repair process is error-prone and results in disruption of the gene, such as a frameshift mutation, e.g., biallelic frameshift mutation, which can result in complete knockout of the gene. For example, in some aspects, the disruption comprises inducing a deletion, mutation, and/or insertion. In some embodiments, the disruption results in the presence of an early stop codon. In some aspects, the presence of an insertion, deletion, translocation, frameshift mutation, and/or a premature stop codon results in disruption of the expression, activity, and/or function of the gene.

In some embodiments, gene disruption is achieved using antisense techniques, such as by RNA interference (RNAi), short interfering RNA (siRNA), short hairpin (shRNA), and/or ribozymes are used to selectively suppress or repress expression of the gene. siRNA technology is RNAi which employs a double-stranded RNA molecule having a sequence homologous with the nucleotide sequence of mRNA which is transcribed from the gene, and a sequence complementary with the nucleotide sequence. siRNA generally is homologous/complementary with one region of mRNA which is transcribed from the gene, or may be siRNA including a plurality of RNA molecules which are homologous/complementary with different regions. In some aspects, the siRNA is comprised in a polycistronic construct. In particular aspects, the siRNA suppresses both wild-type and mutant protein translation from endogenous mRNA.

In some embodiments, the disruption is achieved using a DNA-targeting molecule, such as a DNA-binding protein or DNA-binding nucleic acid, or complex, compound, or composition, containing the same, which specifically binds to or hybridizes to the gene. In some embodiments, the DNA-targeting molecule comprises a DNA-binding domain, e.g., a zinc finger protein (ZFP) DNA-binding domain, a transcription activator-like protein (TAL) or TAL effector (TALE) DNA-binding domain, a clustered regularly interspaced short palindromic repeats (CRISPR) DNA-binding domain, or a DNA-binding domain from a meganuclease. Zinc finger, TALE, and CRISPR system binding domains can be engineered to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 2011/0301073.

In some embodiments, the DNA-targeting molecule, complex, or combination contains a DNA-binding molecule and one or more additional domain, such as an effector domain to facilitate the repression or disruption of the gene. For example, in some embodiments, the gene disruption is carried out by fusion proteins that comprise DNA-binding proteins and a heterologous regulatory domain or functional fragment thereof. In some aspects, domains include, e.g., transcription factor domains such as activators, repressors, co-activators, co-repressors, silencers, oncogenes, DNA repair enzymes and their associated factors and modifiers, DNA rearrangement enzymes and their associated factors and modifiers, chromatin associated proteins and their modifiers, e.g. kinases, acetylases and deacetylases, and DNA modifying enzymes, e.g. methyltransferases, topoisomerases, helicases, ligases, kinases, phosphatases, polymerases, endonucleases, and their associated factors and modifiers. See, for example, U.S. Patent Application Publication Nos. 2005/0064474; 2006/0188987 and 2007/0218528, incorporated by reference in their entireties herein, for details regarding fusions of DNA-binding domains and nuclease cleavage domains. In some aspects, the additional domain is a nuclease domain. Thus, in some embodiments, gene disruption is facilitated by gene or genome editing, using engineered proteins, such as nucleases and nuclease-containing complexes or fusion proteins, composed of sequence-specific DNA-binding domains fused to or complexed with non-specific DNA-cleavage molecules such as nucleases.

In some aspects, these targeted chimeric nucleases or nuclease-containing complexes carry out precise genetic modifications by inducing targeted double-stranded breaks or single-stranded breaks, stimulating the cellular DNA-repair mechanisms, including error-prone nonhomologous end joining (NHEJ) and homology-directed repair (HDR). In some embodiments the nuclease is an endonuclease, such as a zinc finger nuclease (ZFN), TALE nuclease (TALEN), and RNA-guided endonuclease (RGEN), such as a CRISPR-associated (Cas) protein, or a meganuclease.

In some embodiments, a donor nucleic acid, e.g., a donor plasmid or nucleic acid encoding the genetically engineered antigen receptor, is provided and is inserted by HDR at the site of gene editing following the introduction of the DSBs. Thus, in some embodiments, the disruption of the gene and the introduction of the antigen receptor, e.g., CAR, are carried out simultaneously, whereby the gene is disrupted in part by knock-in or insertion of the CAR-encoding nucleic acid.

In some embodiments, no donor nucleic acid is provided. In some aspects, NHEJ-mediated repair following introduction of DSBs results in insertion or deletion mutations that can cause gene disruption, e.g., by creating missense mutations or frameshifts.

1. ZFPs and ZFNs

In some embodiments, the DNA-targeting molecule includes a DNA-binding protein such as one or more zinc finger protein (ZFP) or transcription activator-like protein (TAL), fused to an effector protein such as an endonuclease. Examples include ZFNs, TALEs, and TALENs.

In some embodiments, the DNA-targeting molecule comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion. The term zinc finger DNA binding protein is often abbreviated as zinc finger protein or ZFP. Among the ZFPs are artificial ZFP domains targeting specific DNA sequences, typically 9-18 nucleotides long, generated by assembly of individual fingers.

ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice.

In some aspects, disruption of MeCP2 is carried out by contacting a first target site in the gene with a first ZFP, thereby disrupting the gene. In some embodiments, the target site in the gene is contacted with a fusion ZFP comprising six fingers and the regulatory domain, thereby inhibiting expression of the gene.

In some embodiments, the step of contacting further comprises contacting a second target site in the gene with a second ZFP. In some aspects, the first and second target sites are adjacent. In some embodiments, the first and second ZFPs are covalently linked. In some aspects, the first ZFP is a fusion protein comprising a regulatory domain or at least two regulatory domains.

In some embodiments, the first and second ZFPs are fusion proteins, each comprising a regulatory domain or each comprising at least two regulatory domains. In some embodiments, the regulatory domain is a transcriptional repressor, a transcriptional activator, an endonuclease, a methyl transferase, a histone acetyltransferase, or a histone deacetylase.

In some embodiments, the ZFP is encoded by a ZFP nucleic acid operably linked to a promoter. In some aspects, the method further comprises the step of first administering the nucleic acid to the cell in a lipid:nucleic acid complex or as naked nucleic acid. In some embodiments, the ZFP is encoded by an expression vector comprising a ZFP nucleic acid operably linked to a promoter. In some embodiments, the ZFP is encoded by a nucleic acid operably linked to an inducible promoter. In some aspects, the ZFP is encoded by a nucleic acid operably linked to a weak promoter.

In some embodiments, the target site is upstream of a transcription initiation site of the gene. In some aspects, the target site is adjacent to a transcription initiation site of the gene. In some aspects, the target site is adjacent to an RNA polymerase pause site downstream of a transcription initiation site of the gene.

In some embodiments, the DNA-targeting molecule is or comprises a zinc-finger DNA binding domain fused to a DNA cleavage domain to form a zinc-finger nuclease (ZFN). In some embodiments, fusion proteins comprise the cleavage domain (or cleavage half-domain) from at least one Type liS restriction enzyme and one or more zinc finger binding domains, which may or may not be engineered. In some embodiments, the cleavage domain is from the Type liS restriction endonuclease Fok I. Fok I generally catalyzes double-stranded cleavage of DNA, at 9 nucleotides from its recognition site on one strand and 13 nucleotides from its recognition site on the other.

In some embodiments, ZFNs target a gene present in the engineered cell. In some aspects, the ZFNs efficiently generate a double strand break (DSB), for example at a predetermined site in the coding region of the gene. Typical regions targeted include exons, regions encoding N terminal regions, first exon, second exon, and promoter or enhancer regions. In some embodiments, transient expression of the ZFNs promotes highly efficient and permanent disruption of the target gene in the engineered cells. In particular, in some embodiments, delivery of the ZFNs results in the permanent disruption of the gene with efficiencies surpassing 50%.

Many gene-specific engineered zinc fingers are available commercially. For example, Sangamo Biosciences (Richmond, CA, USA) has developed a platform (CompoZr) for zinc-finger construction in partnership with Sigma-Aldrich (St. Louis, MO, USA), allowing investigators to bypass zinc-finger construction and validation altogether, and provides specifically targeted zinc fingers for thousands of proteins (Gaj et al., Trends in Biotechnology, 2013, 31(7), 397-405). In some embodiments, commercially available zinc fingers are used or are custom designed.

2. TALs, TALEs and TALENs

In some embodiments, the DNA-targeting molecule comprises a naturally occurring or engineered (non-naturally occurring) transcription activator-like protein (TAL) DNA binding domain, such as in a transcription activator-like protein effector (TALE) protein, See, e.g., U.S. Patent Publication No. 2011/0301073, incorporated by reference in its entirety herein.

A TALE DNA binding domain or TALE is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. Each TALE repeat unit includes 1 or 2 DNA-binding residues making up the Repeat Variable Diresidue (RVD), typically at positions 12 and/or 13 of the repeat. The natural (canonical) code for DNA recognition of these TALEs has been determined such that an HD sequence at positions 12 and 13 leads to a binding to cytosine (C), NG binds to T, NI to A, NN binds to G or A, and NO binds to T and non-canonical (atypical) RVDs are also known. See, U.S. Patent Publication No. 2011/0301073. In some embodiments, TALEs may be targeted to any gene by design of TAL arrays with specificity to the target DNA sequence. The target sequence generally begins with a thymidine.

In some embodiments, the molecule is a DNA binding endonuclease, such as a TALE nuclease (TALEN). In some aspects the TALEN is a fusion protein comprising a DNA-binding domain derived from a TALE and a nuclease catalytic domain to cleave a nucleic acid target sequence.

In some embodiments, the TALEN recognizes and cleaves the target sequence in the gene. In some aspects, cleavage of the DNA results in double-stranded breaks. In some aspects the breaks stimulate the rate of homologous recombination or non-homologous end joining (NHEJ). Generally, NHEJ is an imperfect repair process that often results in changes to the DNA sequence at the site of the cleavage. In some aspects, repair mechanisms involve rejoining of what remains of the two DNA ends through direct re-ligation (Critchlow and Jackson, 1998) or via the so-called microhomology-mediated end joining. In some embodiments, repair via NHEJ results in small insertions or deletions and can be used to disrupt and thereby repress the gene. In some embodiments, the modification may be a substitution, deletion, or addition of at least one nucleotide. In some aspects, cells in which a cleavage-induced mutagenesis event, i.e. a mutagenesis event consecutive to an NHEJ event, has occurred can be identified and/or selected by well-known methods in the art.

In some embodiments, TALE repeats are assembled to specifically target a gene. A library of TALENs targeting 18,740 human protein-coding genes has been constructed. Custom-designed TALE arrays are commercially available through Cellectis Bioresearch (Paris, France), Transposagen Biopharmaceuticals (Lexington, KY, USA), and Life Technologies (Grand Island, NY, USA).

In some embodiments the TALENs are introduced as trans genes encoded by one or more plasmid vectors. In some aspects, the plasmid vector can contain a selection marker which provides for identification and/or selection of cells which received said vector.

3. RGENs (CRISPR/Cas Systems)

In some embodiments, the disruption is carried out using one or more DNA-binding nucleic acids, such as disruption via an RNA-guided endonuclease (RGEN). For example, the disruption can be carried out using clustered regularly interspaced short palindromic repeats (CRISPR) and CRISPR-associated (Cas) proteins. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence". In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions.

III. Astrocyte Differentiation Methods

In some embodiments, methods are provided for producing differentiated cells from an essentially single cell suspension of pluripotent stem cells (PSCs), such as human iPSCs. In some embodiments, the PSCs are cultured to pre-confluency to prevent any cell aggregates. In certain aspects, the PSCs are dissociated by incubation with a cell dissociation enzyme, such as exemplified by TRYPSIN™ or TRYPLE™. PSCs can also be dissociated into an essentially single cell suspension by pipetting. In addition, Blebbistatin (e.g., about 2.5 μM) can be added to the medium to increase PSC survival after dissociation into single cells while the cells are not adhered to a culture vessel. A ROCK inhibitor instead of Blebbistatin may alternatively used to increase PSC survival after dissociated into single cells.

Once a single cell suspension of PSCs is obtained at a known cell density, the cells are generally seeded in an appropriate culture vessel, such as a tissue culture plate, such as a flask, 6-well, 24-well, or 96-well plate. A culture vessel used for culturing the cell(s) can include, but is particularly not limited to: flask, flask for tissue culture, dish, petri dish, dish for tissue culture, multi dish, micro plate, micro-well plate, multi plate, multi-well plate, micro slide, chamber slide, tube, tray, CELLSTACK® Chambers, culture bag, and roller bottle, as long as it is capable of culturing the stem cells therein. The cells may be cultured in a volume of at least or about 0.2, 0.5, 1, 2, 5, 10, 20, 30, 40, 50 ml, 100 ml, 150 ml, 200 ml, 250 ml, 300 ml, 350 ml, 400 ml, 450 ml, 500 ml, 550 ml, 600 ml, 800 ml, 1000 ml, 1500 ml, or any range derivable therein, depending on the needs of the culture. In a certain embodiment, the culture vessel may be a bioreactor, which may refer to any device or system ex vivo that supports a biologically active environment such that cells can be propagated. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

In certain aspects, the PSCs, such as iPSCs, are plated at a cell density appropriate for efficient differentiation. Generally, the cells are plated at a cell density of about 10,000 to about 75,000 cells/cm$^2$, such as of about 15,000 to about 40,000 cells/cm$^2$. In a 6 well plate, the cells may be seeded at a cell density of about 50,000 to about 400,000 cells per well. In exemplary methods, the cells are seeded at a cell density of about 100,000, about 150,000, about 200,000, about 250,000, about 300,000 or about 350,000 cells per well, such as about 200,000 cells per well.

The PSCs, such as iPSCs, are generally cultured on culture plates coated by one or more cellular adhesion proteins to promote cellular adhesion while maintaining cell viability. For example, preferred cellular adhesion proteins include extracellular matrix proteins such as vitronectin, laminin, collagen and/or fibronectin which may be used to coat a culturing surface as a means of providing a solid support for pluripotent cell growth. The term "extracellular matrix" is recognized in the art. Its components include one or more of the following proteins: fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin. In exemplary methods, the PSCs are grown on culture plates coated with vitronectin or fibronectin. In some embodiments, the cellular adhesion proteins are human proteins.

The extracellular matrix (ECM) proteins may be of natural origin and purified from human or animal tissues or, alternatively, the ECM proteins may be genetically engineered recombinant proteins or synthetic in nature. The ECM proteins may be a whole protein or in the form of peptide fragments, native or engineered. Examples of ECM protein that may be useful in the matrix for cell culture include laminin, collagen I, collagen IV, fibronectin and vitronectin. In some embodiments, the matrix composition includes synthetically generated peptide fragments of fibronectin or recombinant fibronectin. In some embodiments, the matrix composition is xeno-free. For example, in the xeno-free matrix to culture human cells, matrix components of human origin may be used, wherein any non-human animal components may be excluded.

In some aspects, the total protein concentration in the matrix composition may be about 1 ng/mL to about 1 mg/mL. In some preferred embodiments, the total protein concentration in the matrix composition is about 1 μg/mL to about 300 μg/mL. In more preferred embodiments, the total protein concentration in the matrix composition is about 5 μg/mL to about 200 μg/mL.

Cells can be cultured with the nutrients necessary to support the growth of each specific population of cells. Generally, the cells are cultured in growth media including a carbon source, a nitrogen source and a buffer to maintain pH. The medium can also contain fatty acids or lipids, amino acids (such as non-essential amino acids), vitamin(s), growth factors, cytokines, antioxidant substances, pyruvic acid, buffering agents, and inorganic salts. An exemplary growth medium contains a minimal essential media, such as Dulbecco's Modified Eagle's medium (DMEM) or ESSENTIAL 8™ (E8™) medium, supplemented with various nutrients, such as non-essential amino acids and vitamins, to enhance stem cell growth. Examples of minimal essential media include, but are not limited to, Minimal Essential Medium Eagle (MEM) Alpha medium, Dulbecco's modified Eagle medium (DMEM), RPMI-1640 medium, 199 medium, and F12 medium. Additionally, the minimal essential media may be supplemented with additives such as horse, calf or fetal bovine serum. Alternatively, the medium can be serum free. In other cases, the growth media may contain "knockout serum replacement," referred to herein as a serum-free formulation optimized to grow and maintain undifferentiated cells, such as stem cell, in culture. KNOCKOUT™ serum replacement is disclosed, for example, in U.S. Patent Application No. 2002/0076747, which is incorporated herein by reference. Preferably, the PSCs are cultured in a fully defined and feeder free media.

Accordingly, the PSCs are generally cultured in a fully defined culture medium after plating. In certain aspects, about 18-24 hours after seeding, the medium is aspirated and fresh medium, such as E8™ medium, is added to the culture. In certain aspects, the single cell PSCs are cultured in the fully defined culture medium for about 1, 2 or 3 days after plating. Preferably, the single cells PSCs are cultured in the fully defined culture medium for about 2 days before proceeding with the differentiation process.

In some embodiments, the medium may contain or may not contain any alternatives to serum. The alternatives to serum can include materials which appropriately contain albumin (such as, without limiting, lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolgiycerol, or equivalents thereto. The alternatives to serum can be prepared by the method disclosed in International Publication No. WO 98/30679, for example. Alternatively, any commercially available materials can be used for more convenience. The commercially available materials include KNOCKOUT™ Serum Replacement (KSR), Chemically-defined Lipid concentrated (Gibco), and GLUTAMAX™ (Gibco).

Other culturing conditions can be appropriately defined. For example, the culturing temperature can be about 30 to 40° C., for example, at least or about 31, 32, 33, 34, 35, 36, 37, 38, 39° C. but particularly not limited to them. In one embodiment, the cells are cultured at 37° C. The $CO_2$ concentration can be about 1 to 10%, for example, about 2 to 5%, or any range derivable therein. The oxygen tension can be at least, up to, or about 1, 2, 3, 4, 5, 6, 7, 8, 9, 10, 20%, or any range derivable therein.

The iPSCs, NPC, and/or astrocytes may be cultured in defined media including, but not limited to DMEM-F12, E8, E6, Neurobasal medium, minimal essential medium (MEM), and/or BrainPhys neuronal medium.

A. Neural Progenitor Cells (NPCs)

The iPSCs may differentiated to NPCs with a glial bias, also referred to as glial progenitor cells. The iPSCs may be harvested with EDTA and plated on an extracellular matrix-coated (e.g., MATRIGEL®) surface in Essential 8 medium comprising a ROCK inhibitor (e.g., H1152 at a concentration of 0.1-10 μM, such as 1 μM). The culture may be performed under hypoxic conditions, such as 5% oxygen. Next, the ROCK inhibitor may be removed after 12-48 hours, such as after 24 hours. The cells may then be fed Essential 8 medium for 1-3 days, such as 2 days.

The cells may then be pre-conditioned with media comprising DMEM-F12 and a GSK3 inhibitor (e.g., CHIR99021, such as at a concentration of about 1-5 μM, particularly about 3 μM) under normoxic conditions for about 2-4 days, such as 3 days.

The cells may then be dissociated with TrypLE (Gibco) and aggregates formed using NPC differentiation medium comprising Essential 6 (Gibco), N2 supplement (Gibco) and a ROCK inhibitor (e.g., H1152, such as at a concentration of 0.1-10 μM, such as 1 μM). Aggregates may be formed in ultra-low attachment flasks, spinners (e.g., 500 mL), or bioreactors (e.g., PBS mini bioreactors). The aggregates may be cultured for 5-10 days, such as 8 days, and fed every other day with NPC differentiation medium without ROCK inhibitor. The aggregates may be dissociated with TrypLE for 10-15 minutes in a 37° C. water bath. Dissociated cells may be filtered (e.g., a 100 μM filter) and cryopreserved (e.g., using CryoStorCS10 (BioLifeSolutions)). NPCs may be generated from apparently healthy normal or diseased donors.

The cells may be stained for pluripotency markers SSEA-4 and TRA-1-60 and NPC markers, such as CD24, CD184, and CD271, which start to emerge and increase over time. Additional markers may comprise Nestin and PAX6.

In particular aspects, the present methods do not form neurospheres. In some aspects, the present differentiation methods comprise culture in the absence of SMAD inhibitors, TGFβ inhibitors, and/or γ secretase inhibitors.

B. NPC Differentiation to Astrocytes

Figures 3A, 3B, 3C, 3D, 3E, 3F:
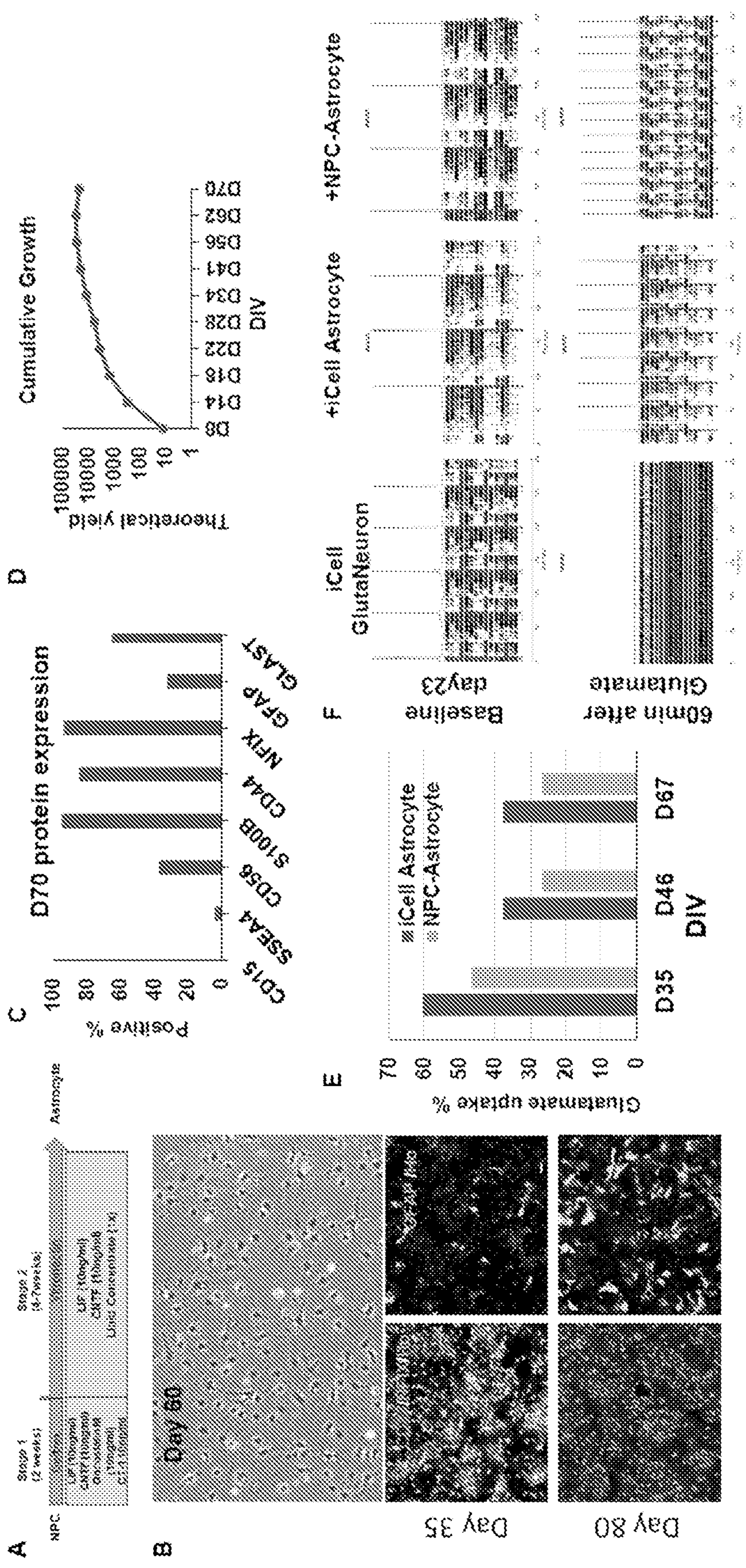
FIGS. 3A-3F: Activation of LIF receptor is sufficient to differentiate astrocytes from NPCs.

A schematic of an exemplary differentiation procedure for generating astrocytes from NPCs is shown in FIG. 3A. NPCs may be seeded at a density of 20 k/cm$^2$ in vessels coated with extracellular matrix protein (e.g., Geltrex) in media comprising DMEM/F12 media supplemented with N2 and B27 (+vitA). The culture may be performed at normoxia, such as at 20% oxygen. The Stage 1 astrocyte media may comprise a chemically defined lipid concentrate (Gibco Catalog No. 11905031, such as at a concentration of 1-5%, particularly about 2%, 3%, or 4%) and epidermal growth factor (e.g., at a concentration of 5-50 ng/mL, particularly about 10, 20, or 30 ng/mL) in combination with Delta Like Canonical Notch Ligand 1 (DLL1) and/or human Jagged 1 Fc chimera protein (JAGG1) (e.g., at a concentration of 1-25 ng/mL, particularly about 10 ng/ml. The Stage 1 astrocyte differentiation media may further comprise one or more LIF receptor ligands, such as Leukemia-Inhibitory Factor protein (LIF), Ciliary-Derived Neurotrophic Factor protein (CNTF), Oncostatin M protein, and/or cardiotrophin 1 (CT-1) (e.g., each a concentration of 1-25 ng/mL, particularly about 10 ng/ml). In particular aspects, the Stage 1 astrocyte media comprises CNTF, oncostatin-M, LIF, and CT-1. The culture may be for about 1-3 weeks, such as about 2 weeks, and passaged upon confluency.

The lipid concentrate may be a concentrated lipid emulsion comprising saturated and unsaturated fatty acids. For example, the lipid concentrate may comprise arachidonic acid (e.g., at a concentration of 2 mg/L), cholesterol (e.g., at a concentration of 220 mg/L), DL-alpha-Tocopherol Acetate (e.g., at a concentration of 70 mg/L), linoleic acid (e.g., at a concentration of 10 mg/L), linolenic acid (e.g., at a concentration of 10 mg/L), myristic acid (e.g., at a concentration of 10 mg/L), oleic acid (e.g., at a concentration of 10 mg/L), palmitic acid (e.g., at a concentration of 10 mg/L), palmitoleic acid (e.g., at a concentration of 10 mg/L), and stearic acid (e.g., at a concentration of 10 mg/L). The lipid concentration may further comprise Tween 80@, Pluronic F-68, and ethyl alcohol.

Next, for Stage 2, the media may be changed to astrocyte media comprising one or more LIF receptor ligands, such LIF, CNTF, Oncostatin M, and/or CT-1, particularly LIF and CNTF. The Stage 2 astrocyte differentiation media may further comprise lipid concentrate. The culture may be for about 3-8 weeks, such as 4-7 weeks, particularly 4 weeks, 5 weeks, 6 weeks, or 7 weeks. The cells may then be stained for astrocyte markers CD44, NFIX and GFAP.

The astrocyte differentiation media (e.g., Stage 1 or Stage 2) may further comprise one or more activators of Notch pathway. The one or more activators of the Notch pathway may be Jagged 1 protein, Jagged 2 protein, and/or Delta-Like protein 1 (DLL1), Delta-Like protein 2 (DLL2), or Delta-Like protein 3 (DLL3).

In specific aspects, the basal media may comprise DMEM/F12, N2 supplement, B27 and retinoic acid supplement (e.g., at a concentration of 1%), GlutaMAX, and penicillin/streptomycin. The astrocyte media may further comprise OSM, CNTF, and LIF (e.g., at a concentration of 5-25 ng/mL, particularly about 10 ng/mL). The astrocyte media may further comprise DLL1 (e.g., at a concentration of 5-50 ng/mL, particularly about 10 ng/mL), JAGG1 (e.g., at a concentration of 5-50 ng/mL, particularly about of 10 ng/mL), lipid concentrate (e.g., at a concentration of 1-5%, particularly about 2%), CT-1 (e.g., at a concentration of 5-50 ng/mL, particularly about 10 ng/mL), and/or EGF (e.g., at a concentration of 5-50 ng/mL, particularly about 20 ng/mL).

Astrocytes express several proteins that can serve as markers for detection by the use of methodologies, such as immunocytochemistry, Western blot analysis, flow cytometry, or enzyme-linked immunoassay (ELISA). Astrocytes may be stained for surface markers, CD44 and glutamate aspartate transporter (GLAST), and intracellular markers, Glial fibrillary acidic protein (GFAP), Excitatory amino acid transporter 1 (EAAT1), Glutamine Synthetase (GS), Aquaporin 4 (AQP4), and S100 calcium-binding protein B (S100β). Cell markers may be detected at the mRNA level, for example, by reverse transcriptase polymerase chain reaction (RT-PCR), Northern blot analysis, or dot-blot hybridization analysis using sequence-specific primers in standard amplification methods using publicly available sequence data (GENBANK®). Expression of tissue-specific markers as detected at the protein or mRNA level is considered positive if the level is at least or about 2-, 3-, 4-, 5-, 6-, 7-, 8-, or 9-fold, and more particularly more than 10-, 20-, 30, 40-, 50-fold or higher above that of a control cell, such as an undifferentiated pluripotent stem cell or other unrelated cell type.

C. Differentiation Media

Cells can be cultured with the nutrients necessary to support the growth of each specific population of cells. Generally, the cells are cultured in growth media including a carbon source, a nitrogen source and a buffer to maintain pH. The medium can also contain fatty acids or lipids, amino acids (such as non-essential amino acids), vitamin(s), growth factors, cytokines, antioxidant substances, pyruvic acid, buffering agents, pH indicators, and inorganic salts. An exemplary growth medium contains a minimal essential media, such as Dulbecco's Modified Eagle's medium (DMEM) or ESSENTIAL 8™ (E8™) medium, supplemented with various nutrients, such as non-essential amino acids and vitamins, to enhance stem cell growth. Examples of minimal essential media include, but are not limited to, Minimal Essential Medium Eagle (MEM) Alpha medium, Dulbecco's modified Eagle medium (DMEM), RPMI-1640 medium, 199 medium, and F12 medium. Additionally, the minimal essential media may be supplemented with additives such as horse, calf or fetal bovine serum. Alternatively, the medium can be serum free. In other cases, the growth media may contain "knockout serum replacement," referred to herein as a serum-free formulation optimized to grow and maintain undifferentiated cells, such as stem cell, in culture. KNOCKOUT™ serum replacement is disclosed, for example, in U.S. Patent Application No. 2002/0076747, which is incorporated herein by reference. Preferably, the PSCs are cultured in a fully-defined and feeder-free media.

In some embodiments, the medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3-thioglycerol, or equivalents thereto. The alternatives to serum can be prepared by the method disclosed in International Publication No. WO 98/30679, for example. Alternatively, any commercially available materials can be used for more convenience. The commercially available materials include KNOCKOUT™ Serum Replacement (KSR), Chemically-defined Lipid concentrated (Gibco), and GLUTAMAX™ (Gibco).

Other culturing conditions can be appropriately defined. For example, the culturing temperature can be about 30 to 40° C., for example, at least or about 31, 32, 33, 34, 35, 36, 37, 38, 39° C. but particularly not limited to them. In one embodiment, the cells are cultured at 37° C. The $CO_2$ concentration can be about 1 to 10%, for example, about 2 to 5%, or any range derivable therein. The oxygen tension can be at least, up to, or about 1, 2, 3, 4, 5, 6, 7, 8, 9, 10, 20%, or any range derivable therein.

D. Cryopreservation

The cells produced by the methods disclosed herein can be cryopreserved, see for example, PCT Publication No. 2012/149484 A2, which is incorporated by reference herein, at any stage of the process, such as NPCs, Stage I astrocytes, or Stage II astrocytes. The cells can be cryopreserved with or without a substrate. In several embodiments, the storage temperature ranges from about −50° C. to about −60° C., about −60° C. to about −70° C., about −70° C. to about −80° C., about −80° C. to about −90° C., about −90° C. to about −100° C. and overlapping ranges thereof. In some embodiments, lower temperatures are used for the storage (e.g., maintenance) of the cryopreserved cells. In several embodiments, liquid nitrogen (or other similar liquid coolant) is used to store the cells. In further embodiments, the cells are stored for greater than about 6 hours. In additional embodiments, the cells are stored about 72 hours. In several embodiments, the cells are stored 48 hours to about one week. In yet other embodiments, the cells are stored for about 1, 2, 3, 4, 5, 6, 7, or 8 weeks. In further embodiments, the cells are stored for 1, 2, 3, 4, 5, 6, 7, 8, 9, 10, 11 or 12 months. The cells can also be stored for longer times. The cells can be cryopreserved separately or on a substrate, such as any of the substrates disclosed herein.

In some embodiments, additional cryoprotectants can be used. For example, the cells can be cryopreserved in a cryopreservation solution comprising one or more cryoprotectants, such as DM80, serum albumin, such as human or bovine serum albumin. In certain embodiments, the solution comprises about 1%, about 1.5%, about 2%, about 2.5%, about 3%, about 4%, about 5%, about 6%, about 7%, about 8%, about 9%, or about 10% DMSO. In other embodiments, the solution comprises about 1% to about 3%, about 2% to about 4%, about 3% to about 5%, about 4% to about 6%, about 5% to about 7%, about 6% to about 8%, about 7% to about 9%, or about 8%• to about 10% dimethylsulfoxide (DMSO) or albumin. In a specific embodiment, the solution comprises 2.5% DMSO. In another specific embodiment, the solution comprises 10% DMSO.

Cells may be cooled, for example, at about 1° C./minute during cryopreservation. In some embodiments, the cryopreservation temperature is about −80° C. to about −180° C., or about −125° C. to about −140° C. In some embodiments, the cells are cooled to 4° C. prior to cooling at about 1° C./minute. Cryopreserved cells can be transferred to vapor phase of liquid nitrogen prior to thawing for use. In some embodiments, for example, once the cells have reached about −80° C., they are transferred to a liquid nitrogen storage area. Cryopreservation can also be done using a controlled-rate freezer. Cryopreserved cells may be thawed, e.g., at a temperature of about 25° C. to about 40° C., and typically at a temperature of about 37° C.

IV. Methods of Use

The present disclosure provides a method by which NPCs and astrocytes can be produced. These cell populations can be used for a number of important research, development, and commercial purposes. These include, but are not limited to, transplantation or implantation of the cells in vivo; screening growth/regulatory factors, pharmaceutical compounds, etc., in vitro; elucidating the mechanism of diseases and infections; studying the mechanism by which drugs and/or growth factors operate; diagnosing and monitoring disease in a patient; gene therapy; and the production of biologically active products, to name but a few.

A. Test Compound Screening

The cell lines produced by the methods disclosed herein may be used in any methods and applications currently known in the art iPSCs or differentiated cells. For example, a method of assessing a compound may be provided, comprising assaying a pharmacological or toxicological property of the compound on the cell line. There may also be provided a method of assessing a compound for an effect on a cell culture, comprising: a) contacting the cell culture provided herein with the compound; and b) assaying an effect of the compound on the cell culture.

The cell culture can be used commercially to screen for factors (such as solvents, small molecule drugs, peptides, oligonucleotides) or environmental conditions (such as culture conditions or manipulation) that affect the characteristics of such cells and their various progeny. For example, test compounds may be chemical compounds, small molecules, polypeptides, growth factors, cytokines, or other biological agents.

In one embodiment, a method includes contacting a cell culture with a test agent and determining if the test agent modulates activity or function of cells within the population. In some applications, screening assays are used for the identification of agents that modulate cell proliferation, alter cell differentiation, or affect cell viability. Screening assays may be performed in vitro or in vivo. Methods of screening and identifying candidate agents include those suitable for high-throughput screening. For example, the cell culture can be positioned or placed on a culture dish, flask, roller bottle or plate (e.g., a single multi-well dish or dish such as 8, 16, 32, 64, 96, 384 and 1536 multi-well plate or dish), optionally at defined locations, for identification of potentially therapeutic molecules. Libraries that can be screened include, for example, small molecule libraries, siRNA libraries, and adenoviral transfection vector libraries.

Other screening applications relate to the testing of pharmaceutical compounds for their effect on retinal tissue maintenance or repair. Screening may be done either because the compound is designed to have a pharmacological effect on the cells, or because a compound designed to have effects elsewhere may have unintended side effects on cells of this tissue type.

B. Therapy and Transplantation

Other embodiments can also provide use of the cell lines for the treatment of a disease or disorder. In another aspect, the disclosure provides a method of treatment of an individual in need thereof, comprising administering a composition comprising engineered cells to said individual.

To determine suitability of cell compositions for therapeutics administration, the cells can first be tested in a suitable animal model. In one aspect, the cell lines are evaluated for their ability to survive and maintain their phenotype in vivo. The compositions are transplanted to immunodeficient animals (e.g., nude mice or animals rendered immunodeficient chemically or by irradiation). Tissues are harvested after a period of growth, and assessed as to whether the pluripotent stem cell-derived cells are still present.

Applicable diseases include but are not limited to autism, RETT syndrome, schizophrenia, Fragile X syndrome, Angelman syndrome, Timothy syndrome, Parkinson's disease, amyotrophic lateral sclerosis, Alzheimer's disease, progressive supranuclear palsy, multiple sclerosis, Huntington's disease, multiple system atrophy, spinocerebellar degeneration, traumatic nerve injury, spinal cord injury, stroke, cerebral hemorrhage, Cerebral thrombosis, cerebral embolism, macular degeneration, tremor, delayed dyskinesia, panic disorder, anxiety disorder, depression, alcoholism, insomnia, mania, Alzheimer's disease, epilepsy, and diabetic neuropathy. In particular aspects, the disease is Alexander's disease or leukodystrophy.

C. Pharmaceutical Compositions

Also provided herein are pharmaceutical compositions and formulations comprising the present cells and a pharmaceutically acceptable carrier. In some aspects, the present composition provides astrocyte cell populations with at least express SSEA4 and CD44.

Cell compositions for administration to a subject in accordance with the present invention thus may be formulated in any conventional manner using one or more physiologically acceptable carriers comprising excipients and auxiliaries which facilitate processing of the compounds into preparations which can be used pharmaceutically. Proper formulation is dependent upon the route of administration chosen.

Pharmaceutical compositions and formulations as described herein can be prepared by mixing the active ingredients (such as cells) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

D. Distribution for Commercial, Therapeutic, and Research Purposes

In some embodiments, a reagent system is provided that includes cells that exists at any time during manufacture, distribution or use. The kits may comprise any combination of the cells described in the present disclosure in combination with undifferentiated pluripotent stem cells or other differentiated cell types, often sharing the same genome. Each cell type may be packaged together, or in separate containers in the same facility, or at different locations, at the same or different times, under control of the same entity or different entities sharing a business relationship. Pharmaceutical compositions may optionally be packaged in a suitable container with written instructions for a desired purpose, such as the mechanistic toxicology.

In some embodiments, a kit that can include, for example, one or more media and components for the production of cells is provided. The reagent system may be packaged either in aqueous media or in lyophilized form, where appropriate. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The components of the kit may be provided as dried powder(s). When reagents and/or components are provided as a dry powder, the powder can be reconstituted by the addition of a suitable solvent. It is envisioned that the solvent may also be provided in another container means. The kits of the present disclosure also will typically include a means for containing the kit component(s) in close confinement for commercial sale. Such containers may include injection or blow molded plastic containers into which the desired vials are retained. The kit can also include instructions for use, such as in printed or electronic format, such as digital format.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation of Astrocytes

Human induced pluripotent stem cells (hiPSCs) were harvested with EDTA, plated on Matrigel (Corning) coated tissue culture (TC)-treated plates at 15,000c/cm$^2$ in Essential 8 medium (Gibco) containing 1 μM ROCK inhibitor H1152 (Sigma), and cultured under hypoxic conditions. The ROCK inhibitor was removed on day 1 and the cells were fed Essential 8 medium for 2 days. Starting on day 3 the cells were preconditioned with media consisting of DMEM-F12 (Gibco) and 3 μM CHIR99021 (Stemgent) and cultured under normoxic conditions. After 3 days the cells were dissociated with TrypLE (Gibco) and aggregates were formed using NPC differentiation medium consisting of Essential 6 (Gibco), N2 supplement (Gibco) and H1152 (1 μM) (FIG. 1). Aggregates were formed in ultra-low attachment flasks, 500 mL spinners, or PBS mini bioreactors. The aggregates were cultured for 8 days and fed every other day with NPC differentiation medium without H1152. On day 14, the aggregates were dissociated with TrypLE for 10-15 minutes in a 37° C. water bath. Dissociated cells were 100 μM filtered and cryopreserved using CryoStorCS10 (BioLifeSolutions). NPCs were generated from 5 different hPSC lines from both apparently healthy normal and diseased donors.

Figures 2A, 2B:
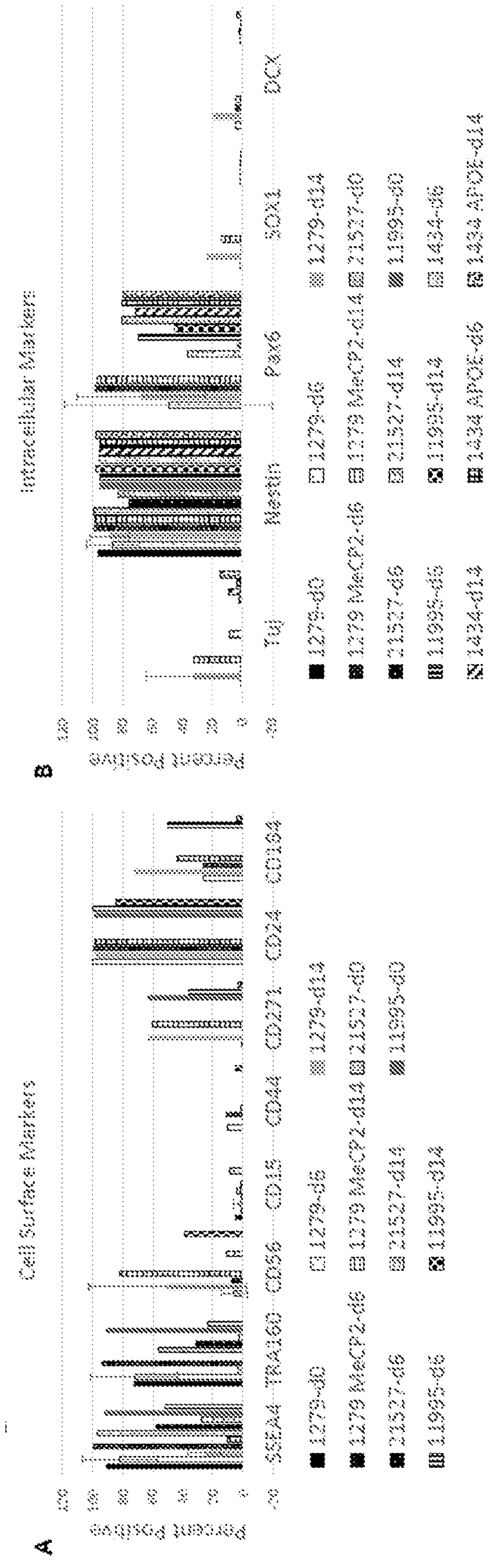
FIGS. 2A-2D: NPC Characterization by flow cytometry. Cells were stained for both cell surface (FIGS. 2A and 2C) and intracellular antigens (FIGS. 2B-2D). Pluripotency markers SSEA-4 and TRA-1-60 were significantly reduced during the 14 day differentiation process while neural progenitor cell (NPC) markers such as CD24, CD184, and CD271 start to emerge and increase over time throughout the differentiation. NPCs from all 5 lines tested showed high expression of the neural progenitor markers Pax6 and Nestin. Expression of the neural progenitor markers SOX1, Doublecortin (DCX) and the pan-neuron marker β3-tubulin (Tuj) was observed in donors 1279 and 1279 MeCP2 but was low or absent in the lines 11995, 21527, 1434, and 1434 APOE.
Figure 2C:
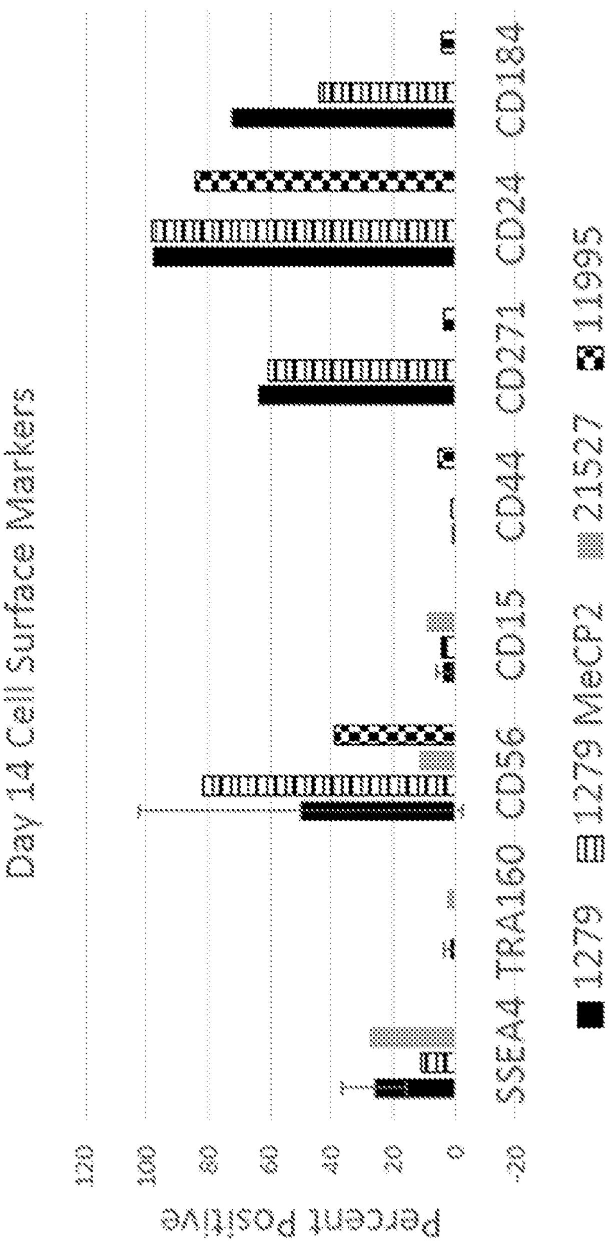
Figure 2D:
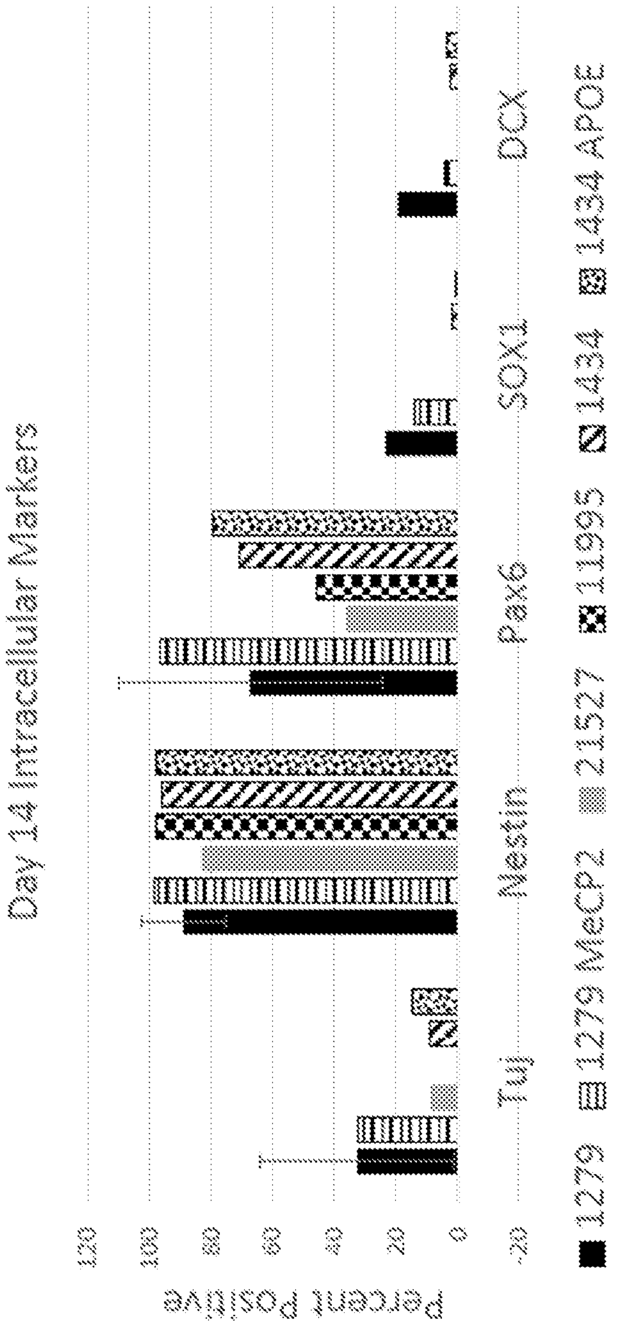

The cells were stained for both cell surface (FIGS. 2A and 2C) and intracellular antigens (FIGS. 2B-2D). Pluripotency markers SSEA-4 and TRA-1-60 were significantly reduced during the 14 day differentiation process while NPC markers such as CD24, CD184, and CD271 start to emerge and increase over time. NPCs from all 5 lines tested showed high Pax6 and Nestin expression while the highest expression of SOX1, Doublecortin (DCX) and 03-tubulin (Tuj) was observed in donor 1279. Cells were dissociated with Accutase (Gibco) for 5 minutes and quenched with medium containing B27 supplement (Gibco). For cell surface antigens 100,000 cells were stained with antibody dilutions for 30 minutes at room temperature. Propidium Iodide (Sigma) was used to exclude dead cells. For intracellular antigens 100,000 cells were first stained for viability using Fixable Viability Stain 620 (BD Biosciences) for 10 minutes followed by fixation with 4% formaldehyde (Sigma) for 15 minutes. Cells were permeabilized with 0.1% triton (Sigma) or 0.1% saponin (MP Biomedicals) and stained with antibody dilutions overnight. Cells were analyzed using an Accuri C6 flow cytometer (BD Biosciences).

A schematic of the differentiation procedure for generating astrocytes from NPCs is shown in FIG. 3A. NPCs were seeded at a density of 20 k/cm$^2$ in vessels coated with Geltrex and fed using DMEM/F12 media supplemented with N2 and B27 (+vitA) and LIF receptor ligands (LIF, CNTF, Oncostatin-M and CT-1, all at 10 ng/ml) for two weeks and passaged upon confluency. After two weeks, media were changed to the LIF+CNTF and lipid concentrate for the rest of differentiation. Cells were fixed in 4% Paraformaldehyde (Sigma) for 60 minutes and stored in DPBS (Gibco) for immunocytochemistry. Primary antibodies were diluted in ICC Permeation Buffer (DPBS+2% FBS+0.2% Triton X-100) and incubated overnight at 4° C. After primary antibody incubation, antibodies were removed and cells were washed 3× in 100 μL DPBS per well for 10 minutes. Secondary antibodies were then applied for one hour at RT. After secondary incubation, Hoescht 33342 (Invitrogen Cat #H3570) was added for 10 minutes. Cells were then washed 3× in 100 μL DPBS per well for 10 minutes and imaged on a Molecular Devices Image Xpress automated microscope. Phase contrast image of cells at day 60 plated on PLO/Laminin substrate (B top) and ICC staining for astrocyte markers CD44, NFIX and GFAP proteins at day 35 and day 80 post differentiation is shown in FIG. 3B. Quantification of percentage of positive cells for several astrocyte markers at day 70 using flow cytometry is shown in FIG. 3C.

The theoretical cumulative yield over the differentiation process showed significant cell growth (FIG. 3D). Time-course glutamate uptake efficacy (the percentage of glutamate concentration in −TBOA sample over the corresponding +TBOA sample) is shown in FIG. 3E. NPC-derived astrocytes could uptake glutamate from media comparable to the iCell Astrocytes. For the glutamate uptake assay, cells were plated in triplicate for both control and +TBOA (Tocris Cat #1223) conditions on vitronectin-coated 96-well plates at a density of 30,000 cells per well. Cells were then cultured for 7 or 14 days before beginning the assay. On day of assay, cells were washed 1× with HBSS (Gibco) and incubated in either HBSS or HBSS+300 μM TBOA for one hour at 37° C. 5% $CO_2$. After incubation, 20 μM glutamate was added to wells incubated with HBSS and 20 μM glutamate+300 μM TBOA was added to wells containing HBSS+300 μM TBOA for one hour at 37° C. 5% $CO_2$. After incubation, the samples were removed to a separate 96-well plate and centrifuged at 400×G for 10 minutes. After centrifugation, the remaining glutamate concentrations in samples were analyzed using the Glutamate-Glo Assay kit (Promega Cat #J7021) following the manufacturer's instructions.

Microelectrode assay (MEA) roster plots of different cultures before (baseline) and after glutamate application are shown in FIG. 3F. Results showed that both iCell astrocytes and NPC-astrocytes were able to maintain network activity and uptake excess glutamate and protect neurons. To further evaluate the function of derived astrocytes, the electrical activities of the astrocyte-neuron co-culture were compared with neuron monoculture on MEA. Briefly, 120K of iCell Gluta Neuron were dotted with 30K of either iCell astrocytes or NPC-astrocytes on 48 classic MEA plates (Axion Biosystems). Cells were fed using BrainPhys complete media and recorded. On the day of recording, 50% of the spent medium was replaced with complete BrainPhys medium approximately 2-4 hours before data acquisition and recorded for 5-10 minutes (300-600 seconds) to adequately capture network bursting behavior. On day 23, neuronal activity was recorded as a baseline and then 20 uM of 1-glutamate was added to the 4 wells for each of three groups (iCell Gluta Neuron alone, iCell Gluta Neuron cocultured with iCell astrocytes and iCell Gluta Neuron co-cultured with NPC derived astrocytes) and recorded again after one hour.

Figure 4A:
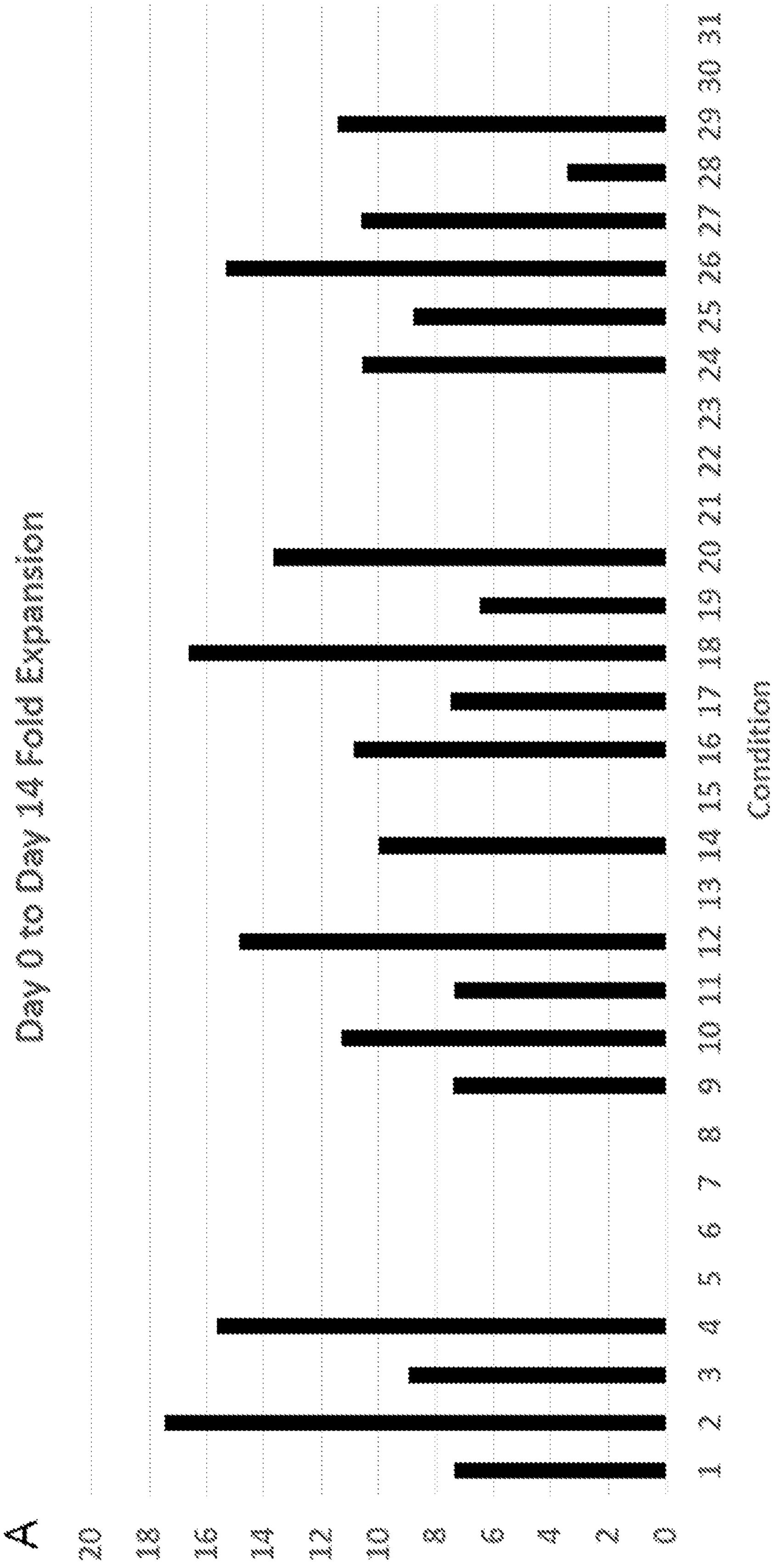
Figure 4B:
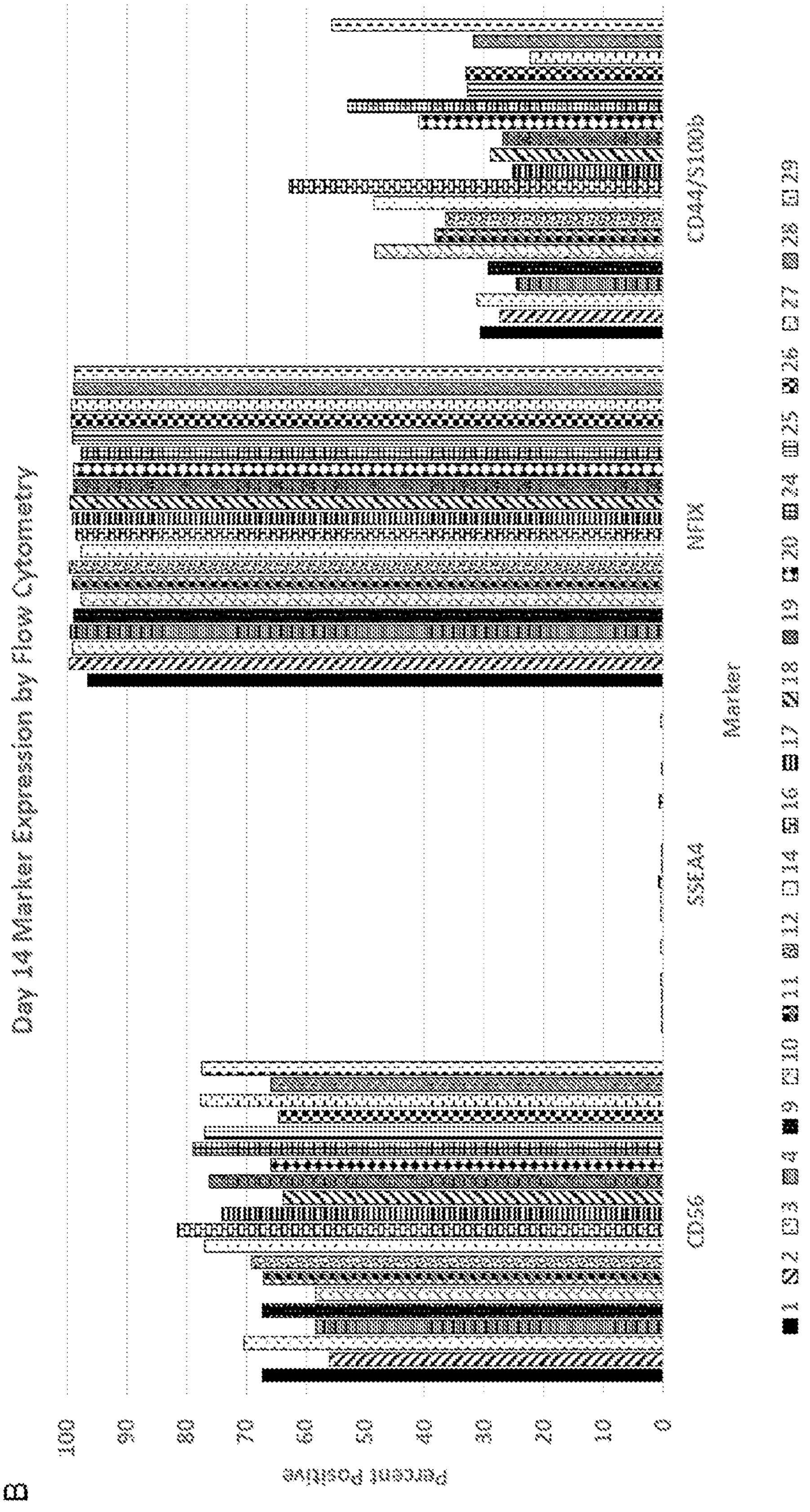

Next, 31 media compositions were evaluated. Fold expansion analysis of the 31 media matrix over 14 days of differentiation time-course is shown in FIG. 4A. Day 14 purity analysis on astrocyte lineage related marker expression by flow cytometry is shown in FIG. 4B. FIG. 4C provides the composition of 11 media which had the best performance based on expansion and purity in the 31 media comparison which were selected for further experimentation.

Figure 5A:
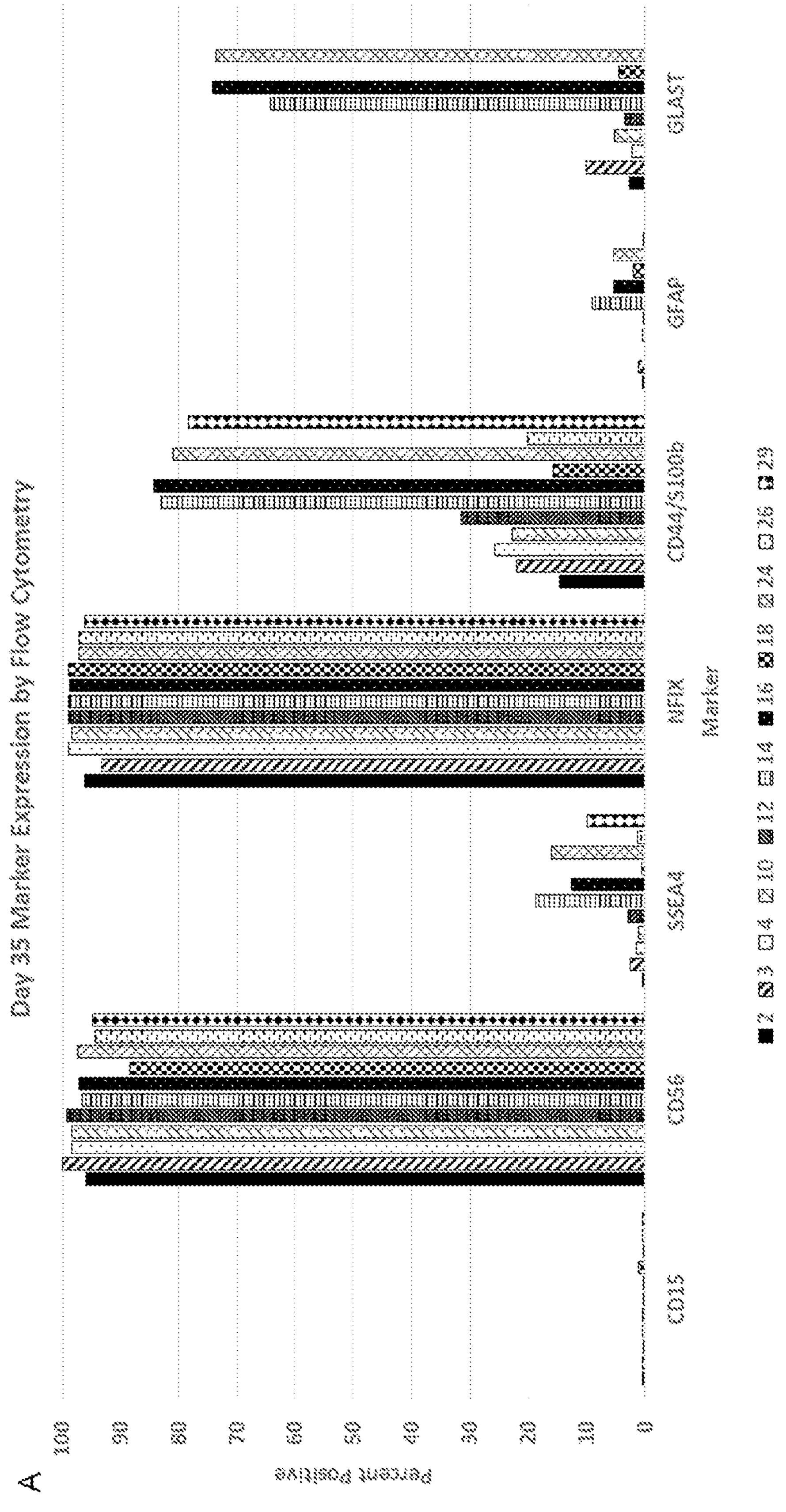
Figure 5B:
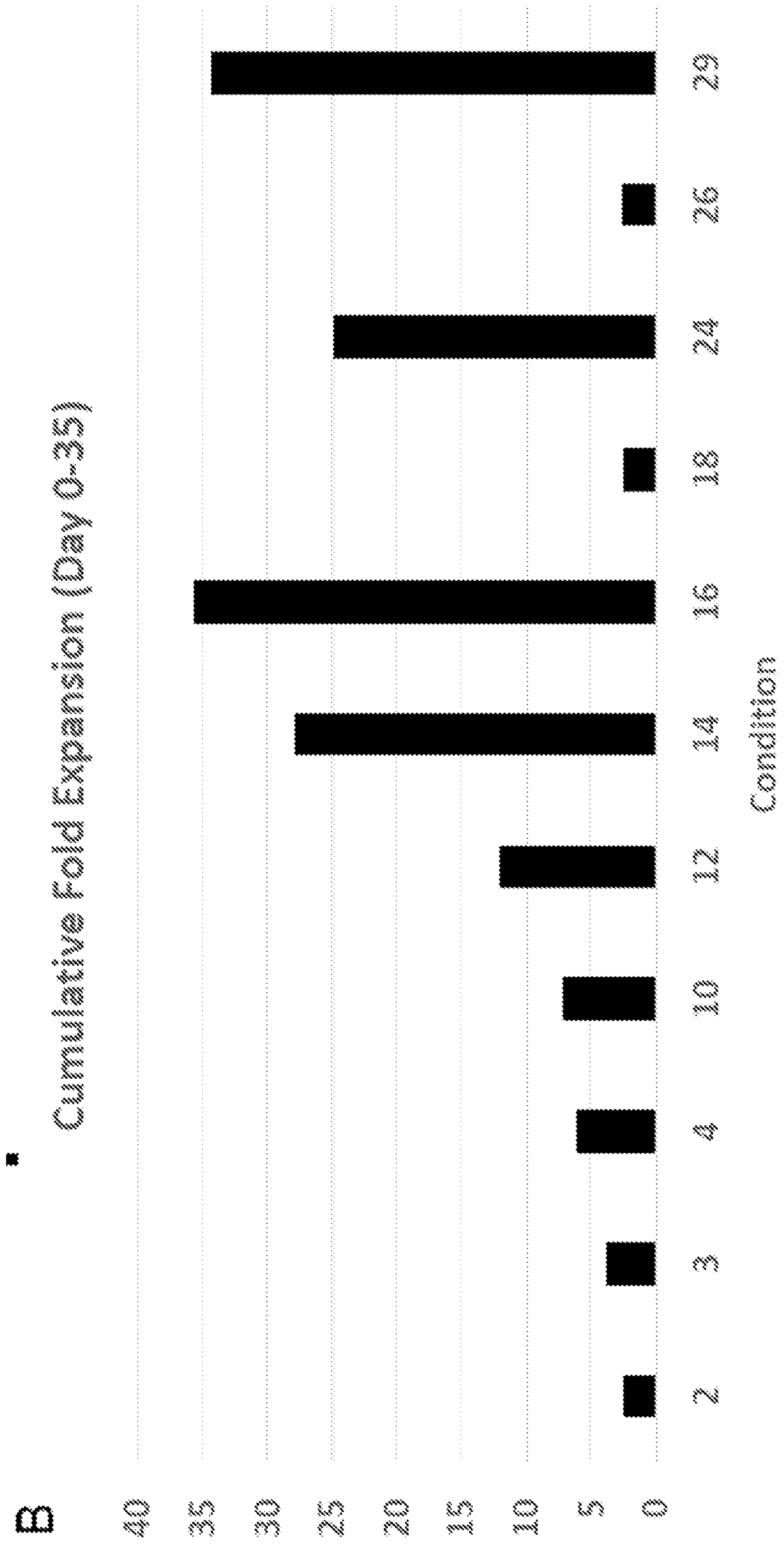
Figure 5C:
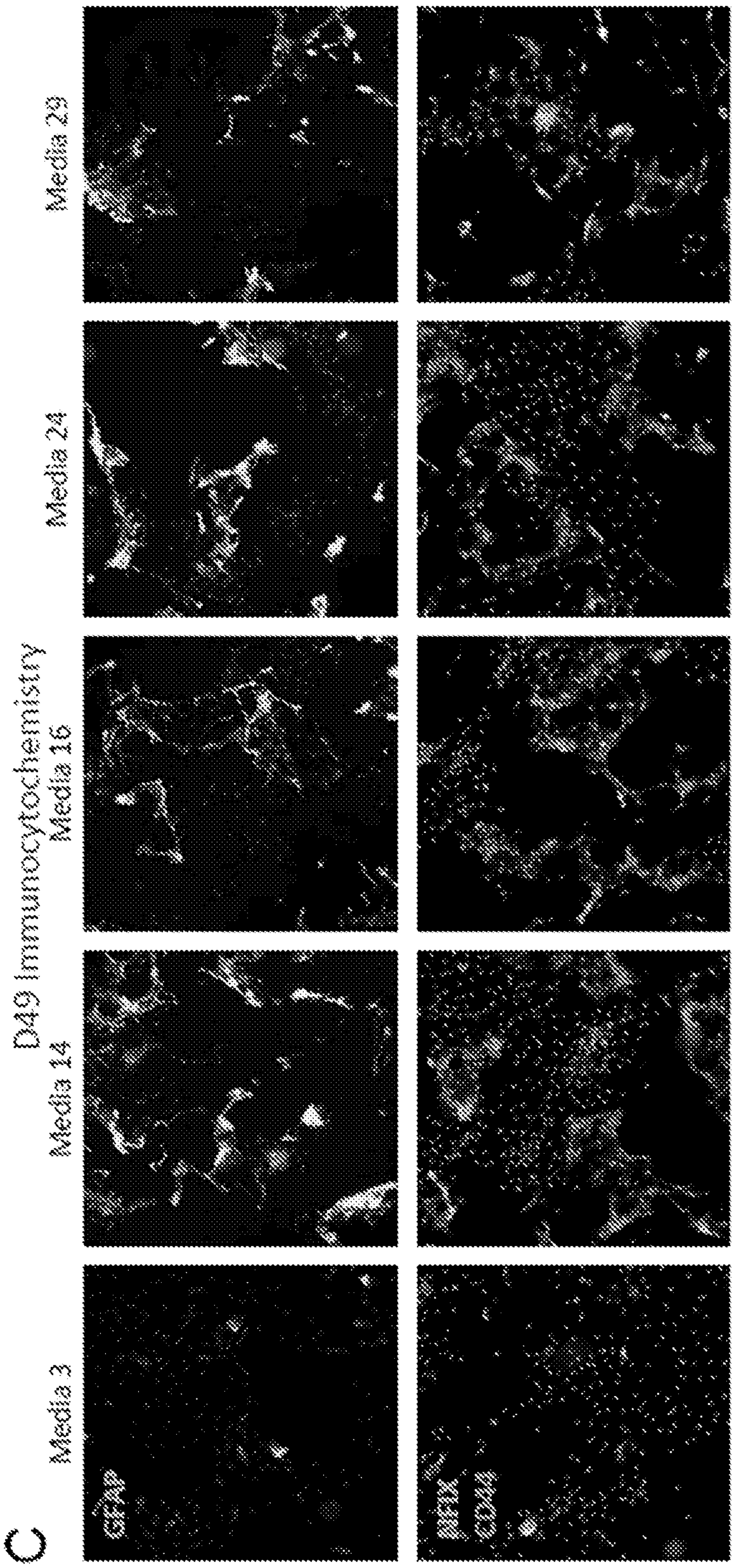
Figure 5D:
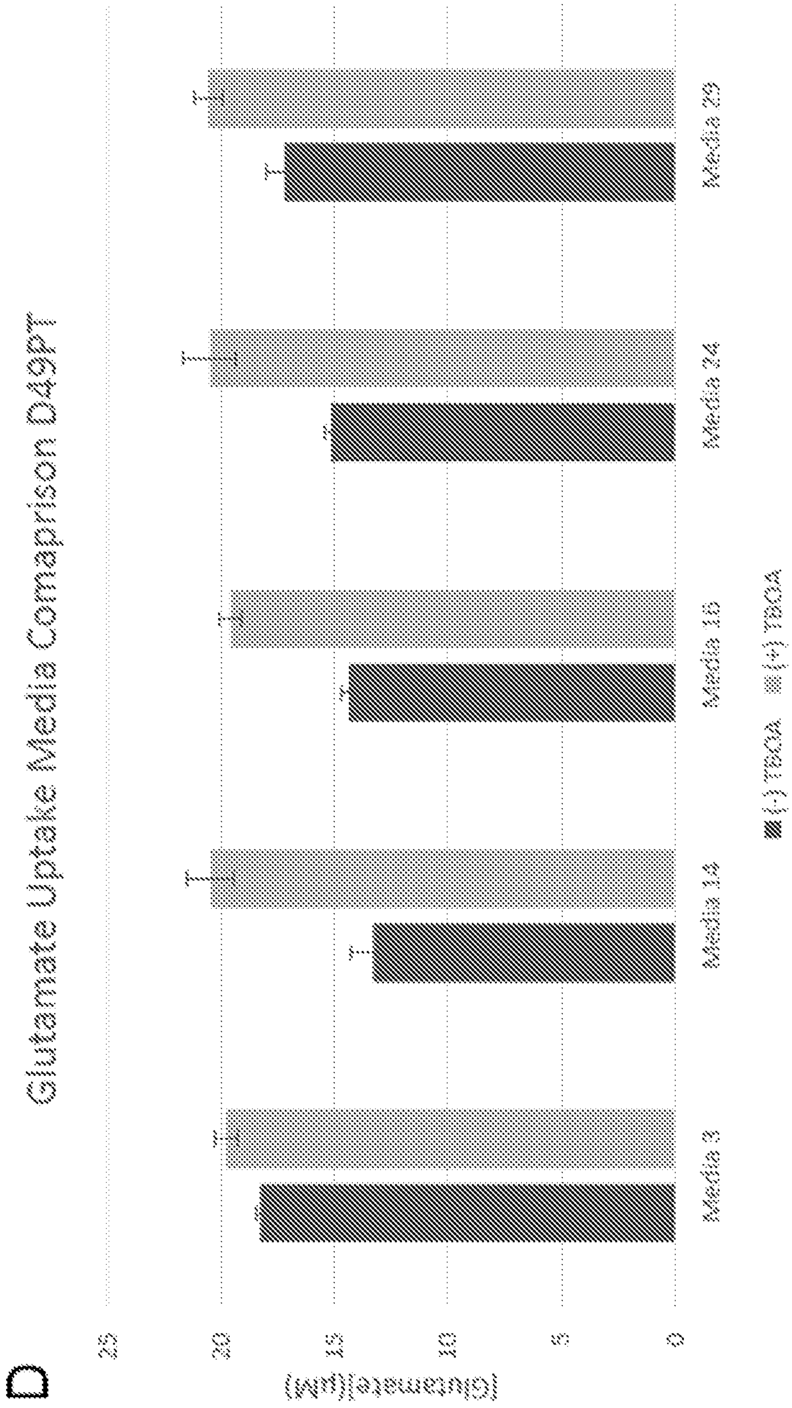

FIG. 5A shows marker expression at Day 35 of differentiation. The cells had less than 1% expression of CD15, about 90-100% expression of CD56 (e.g., over 95%, 96%, 97%, 98%, or 99%), less than 20% expression of SSEA4 (e.g., less than 15%, 10%, 5%, or 1%), about 90-100% expression of NFIX (e.g., over 95%, 96%, 97%, 98%, or 99%), and less than 10% expression of GFAP (e.g., less than 5% or 1%). Expression of CD44/S100b varied from about 15% to over 80% as did the expression of GLAST from about 2% to over 70%. A flow cytometry analysis of the 11 media comparison is shown in FIG. 5B. and cumulative fold expansion analysis of the 11 media matrix over 35 days of differentiation is shown in FIG. 5C. Condition 14 showed an about 28-fold expansion, condition 16 showed an about 36-fold expansion, and condition 29 showed an about 34-fold expansion. The 5 media matrix (FIG. 5E) were further evaluated by immunocytochemistry of D49 cells (FIG. 5E). A glutamate uptake assay of D49 cells from the 5 media comparison study was then performed (FIG. 5D).

Figure 6A:
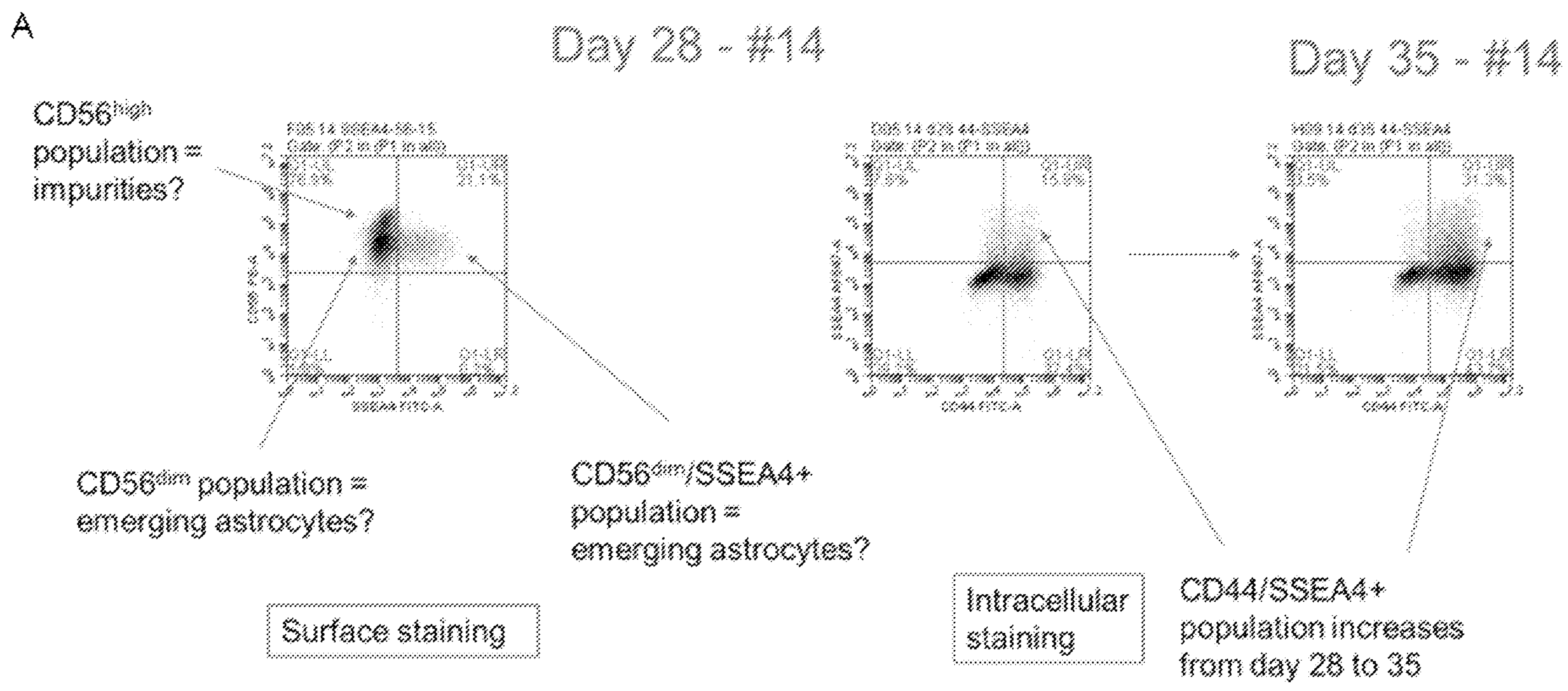
FIGS. 6A-6J: Re-emergence of SSEA4+ as an astrocyte progenitor marker.
Figures 6B, 6C, 6D, 6E, 6F:
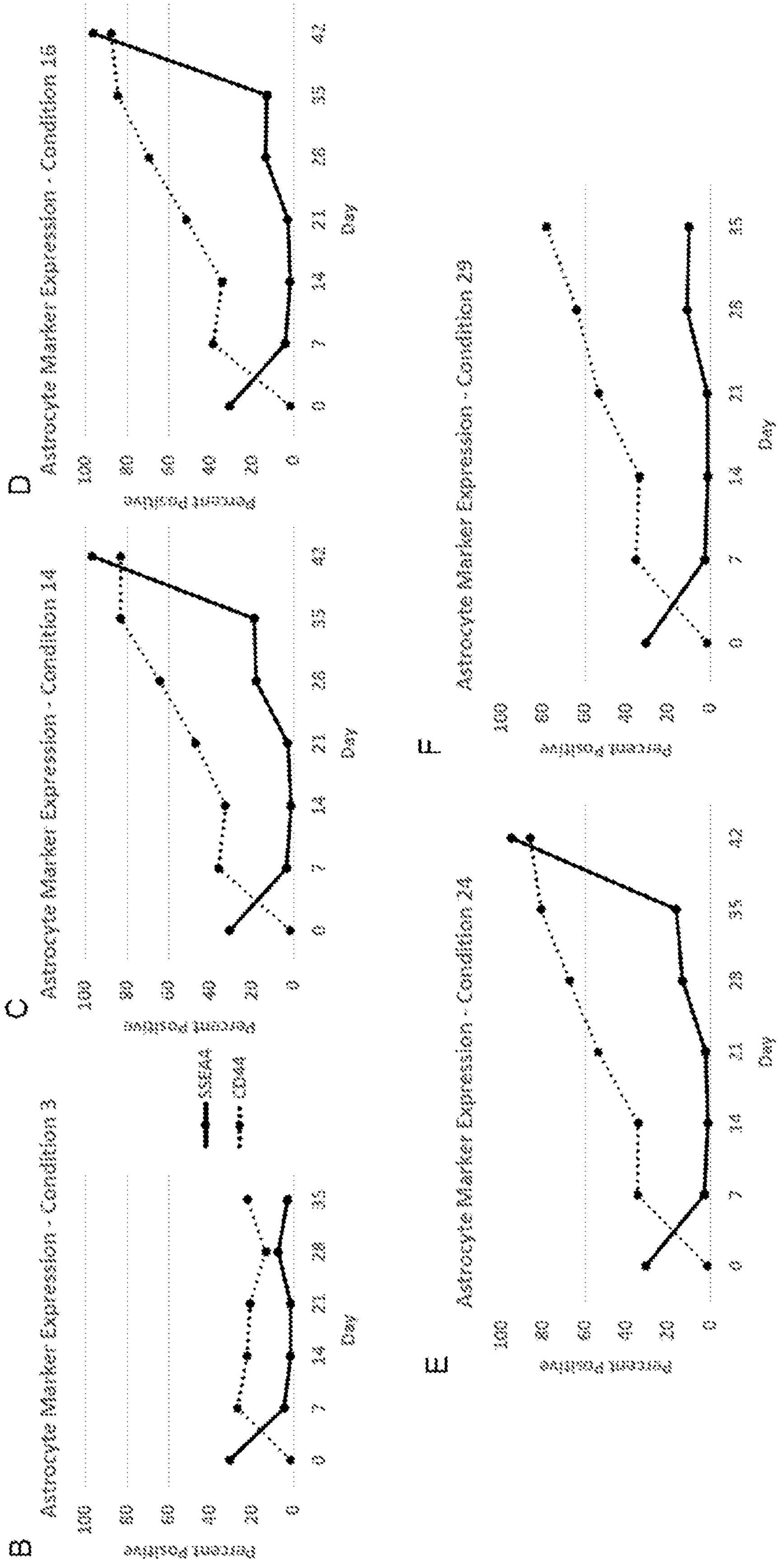
Figures 6G, 6H, 6I, 6J:
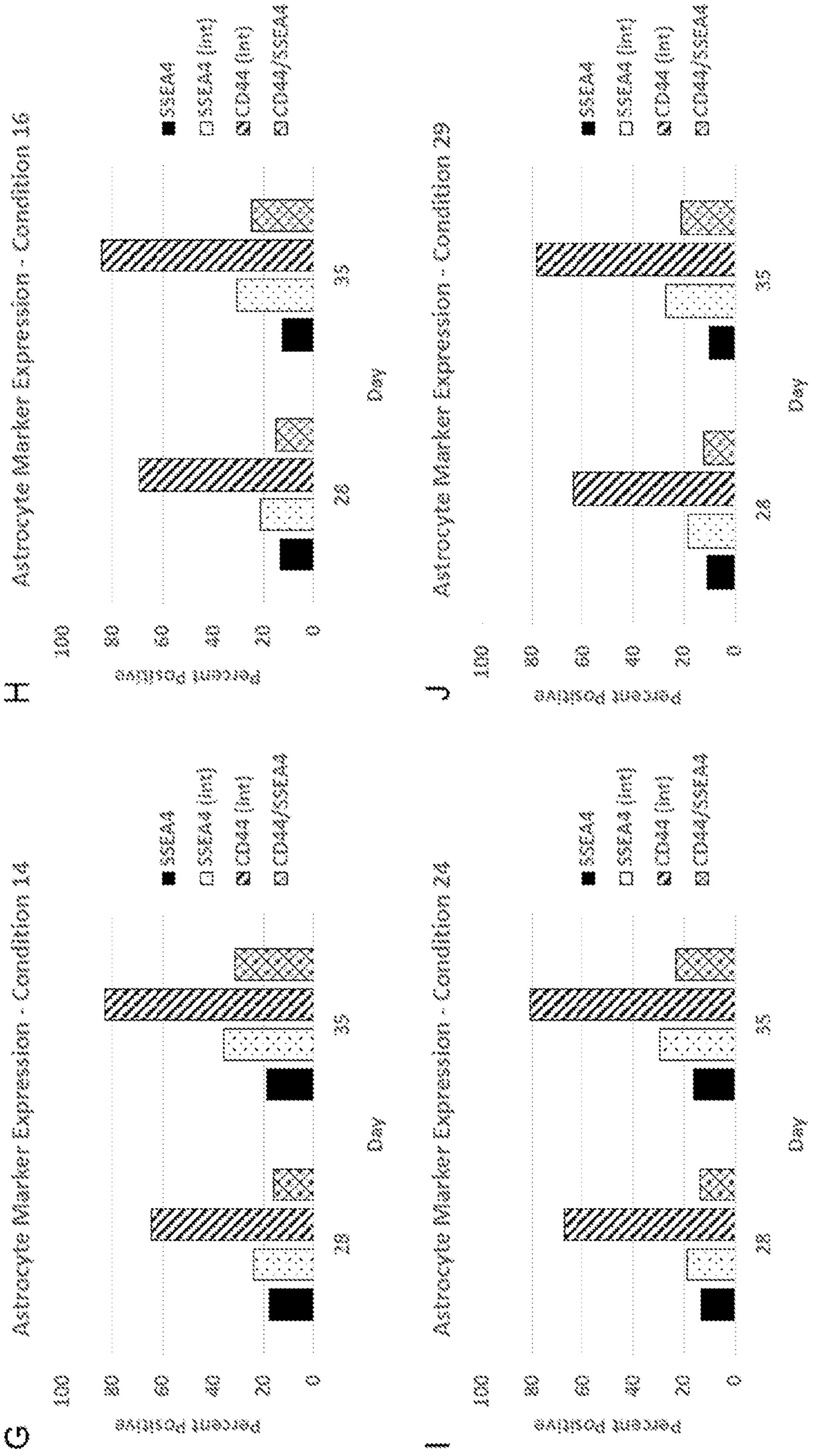

Further studies showed the re-emergence of SSEA4+ as an astrocyte progenitor marker. Representative flow cytometry plots of surface CD56/SSEA4 co-staining on D28 and intracellular CD44/SSEA4 co-staining on both D28 and D35 from media 14 conditions are shown in FIG. 6A. CD44/SSEA4 cells increased from 15.8% on day 28 to 31.3% on day 35 with condition 14. Time courses are shown for surface SSEA4 expression and intracellular CD44 expression from D7 to D35 for (FIG. 6B) condition 3, (FIG. 6C) condition 14, (FIG. 6D) condition 16, (FIG. 6E) condition 24, and (FIG. 6F) condition 29. Media conditions 14, 16 and 24 were continued to D42. Conditions 14, 16, and 24 resulted in an increase of SSEA4 from less than 20% to over 95% after Day 35 as well as a gradual increase of CD44 from about 40% on Day 14 to over 80% on Day 35. Differential expression of SSEA4 and CD44 from surface and intracellular staining on D28 and D35 was measured. A summary of expression profiles of (FIG. 6G) condition 14, (FIG. 6H) condition 16, (FIG. 6I) condition 24, and (FIG. 6J) condition 29 are provided. SSEA4 positive cells were over 60% on Day 28 and over 80% on Day 35 for conditions 14, 16, and 24. CD44/SSEA4 positive cells were about 20-40%, such as about 25%-30%.

Figures 7A, 7B, 7C:
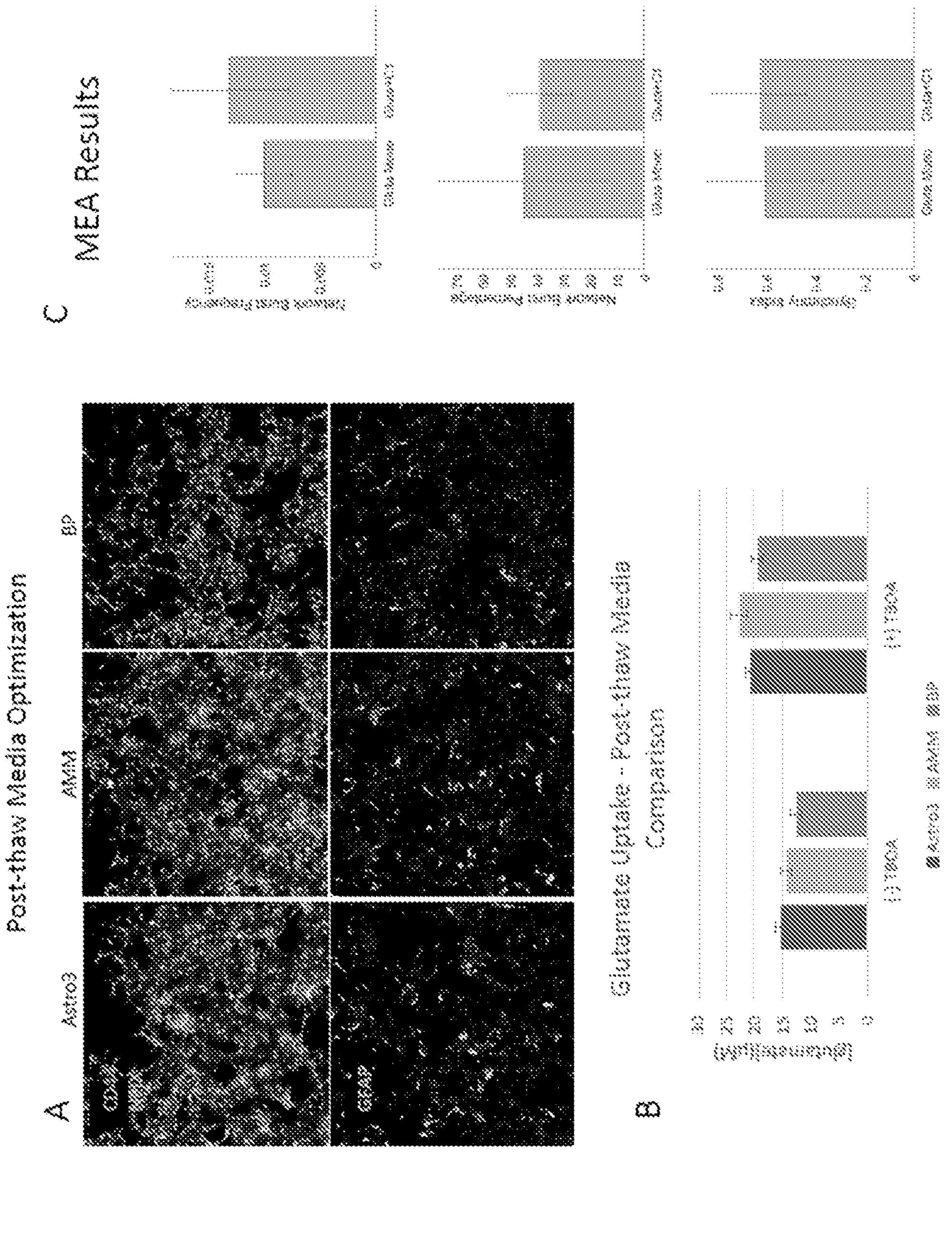
FIGS. 7A-7C: Post Thaw Optimizations and Functional Assays.

Immunocytochemistry of 7 day post-thaw astrocytes cultured in either Astro3 media, AMM or BrainPhys Complete media is shown in FIG. 7A. Glutamate uptake assay of 7 day post-thaw astrocytes cultured in either Astro3 media, AMM or BrainPhys Complete media is shown in FIG. 7C. Quantified results from the MEA data analysis are shown in FIG. 7C.

To further evaluate the function of derived astrocytes, the electrical activities of the astrocyte-neuron co-culture were compared with neuron monoculture on MEA. Luminex analysis of common astrocyte secreted protein concentrations is shown in FIG. 7D. Luminex analysis of cytokine or LPS induced reactive astrocyte secreted protein concentrations is shown in FIG. 7E and RNA-Seq analysis of common astrocyte markers is shown in FIG. 7F.

TABLE 1

Antibody list.

| Antibody | Vendor | Catalog Number |
|---|---|---|
| SSEA4 | BDBioSciences | 560796 |
| TRA160 | Biolegend | 330614 |
| CD56 | BDBioSciences | 555516 |
| CD15 | Biolegend | 301908 |
| CD44 | BDBioSciences | 555478 |
| CD44 | BDBioSciences | 559942 |
| CD271 | Miltenyi Biotec | 130-113-421 |
| CD24 | Biolegend | 311110 |
| CD184 | Biolegend | 306506 |
| TUJ | BDBioSciences | 560381 |
| Nestin | BDBioSciences | 560393 |
| Pax6 | Miltenyi Biotec | 130-123-267 |
| Pax6 | Biolegend | 901301 |
| SOX1 | BDBioSciences | 562224 |
| DCX | BDBioSciences | 561505 |
| NFIX | ThermoFisher | PA5-64917 |
| GFAP | Dako | Z0334 |

Figure 8A:
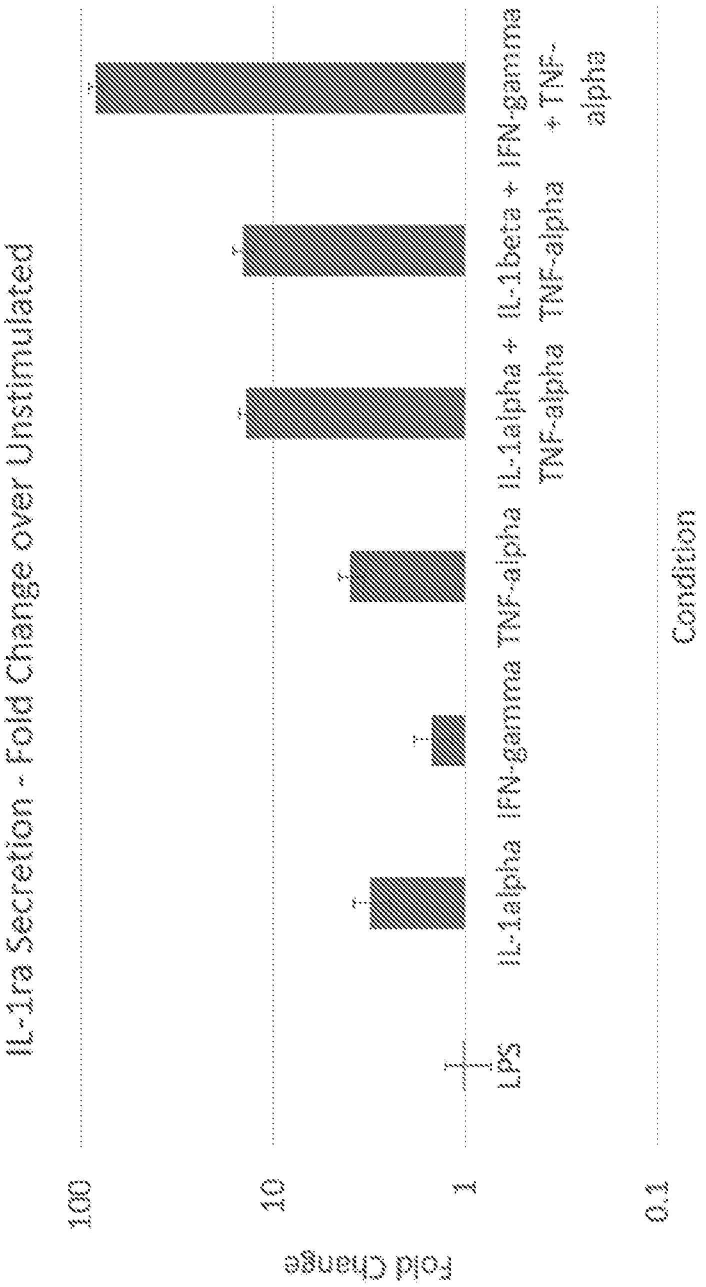
FIGS. 8A-8J: Astrocytes from four lots were thawed and cultured for 7 days in Astro 3 media, before stimulation in basal medium for 24 hours. Supernatant was collected and assayed using a custom Luminex assay from R&D on the FLEXMAP 3D instrument, according to manufacturer's instructions. Each condition was run in duplicate, with the average of all four lots compared to the control (unstimulated) condition to calculate fold change. Error bars are +/−1 SEM.

Astrocytes from four lots were thawed and cultured for 7 days in Astro 3 media, before stimulation in basal medium for 24 hours. Supernatant was collected and assayed using a custom Luminex assay from R&D on the FLEXMAP 3D instrument, according to manufacturer's instructions. Astrocytes were capable of robust secretion of IL-1ra after stimulation with IL-1alpha, IFN-gamma, TNF-alpha or combinations thereof (FIG. 8A). Stimulation with IL-1alpha or TNF-alpha resulted in over a three-fold induction of IL-1ra secretion. TNF-alpha combined with IL-1alpha or IL-1beta resulted in an increase of approximately 14-fold over unstimulated control. The combination of IFN-gamma with TNF-alpha produced the highest fold-change over control, with over 84-fold secretion of IL-1ra compared to control. IL-1ra binds to cell surface IL-1 receptors, blocking binding of pro-inflammatory IL-1alpha and IL-1beta.

Figure 8B:
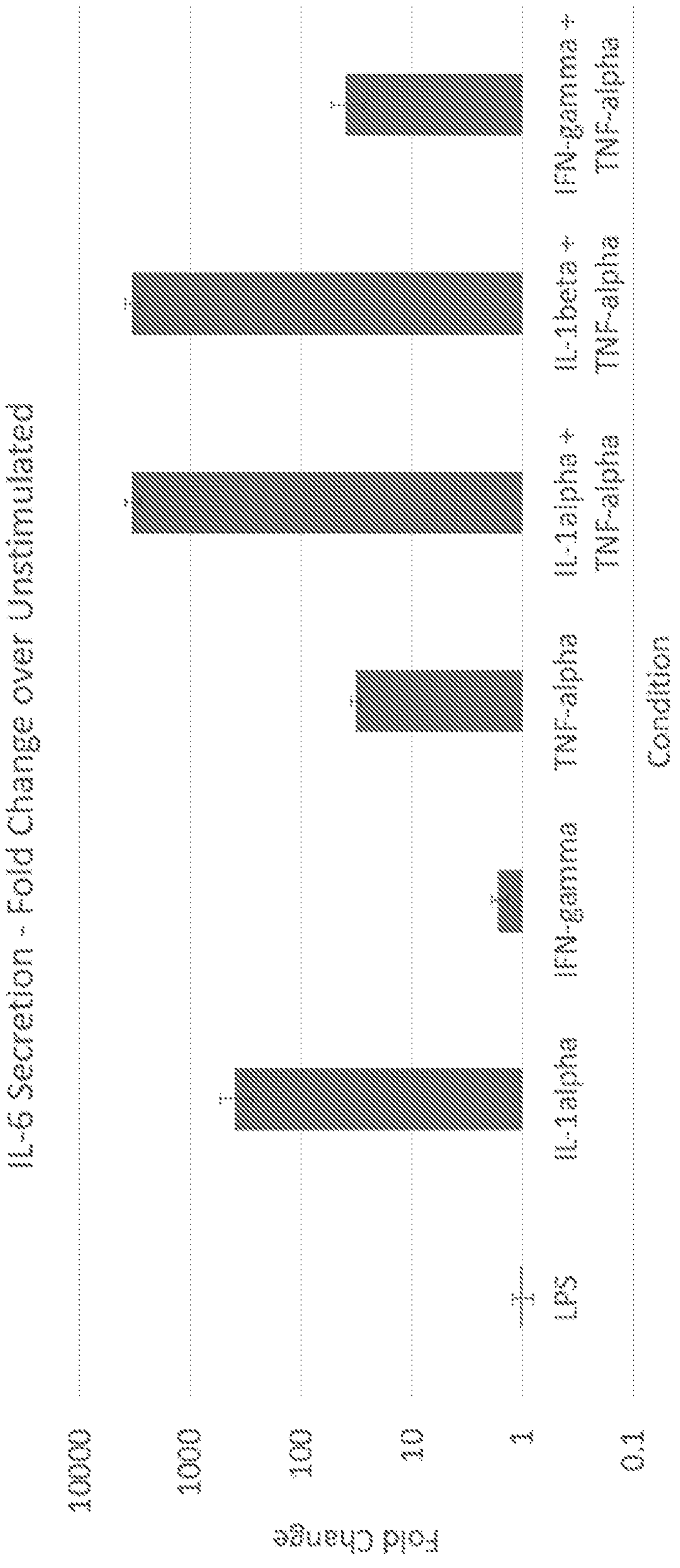

Astrocytes were capable of robust secretion of IL-6 after stimulation with IL-1alpha, TNF-alpha or combinations thereof (FIG. 8B). IFN-gamma alone or combined with TNF-alpha resulted in increased secretion of IL-6 by 32- and 39-fold, respectively, over unstimulated control. IL-alpha stimulation resulted in over 400-fold increase of IL-6 secretion compared to control. TNF-alpha combined with either IL-1alpha or IL-1beta increased IL-6 secretion by over 3300-fold compared to control. IL-6 attracts pro-inflammatory T cells and promotes demyelination.

Figure 8C:
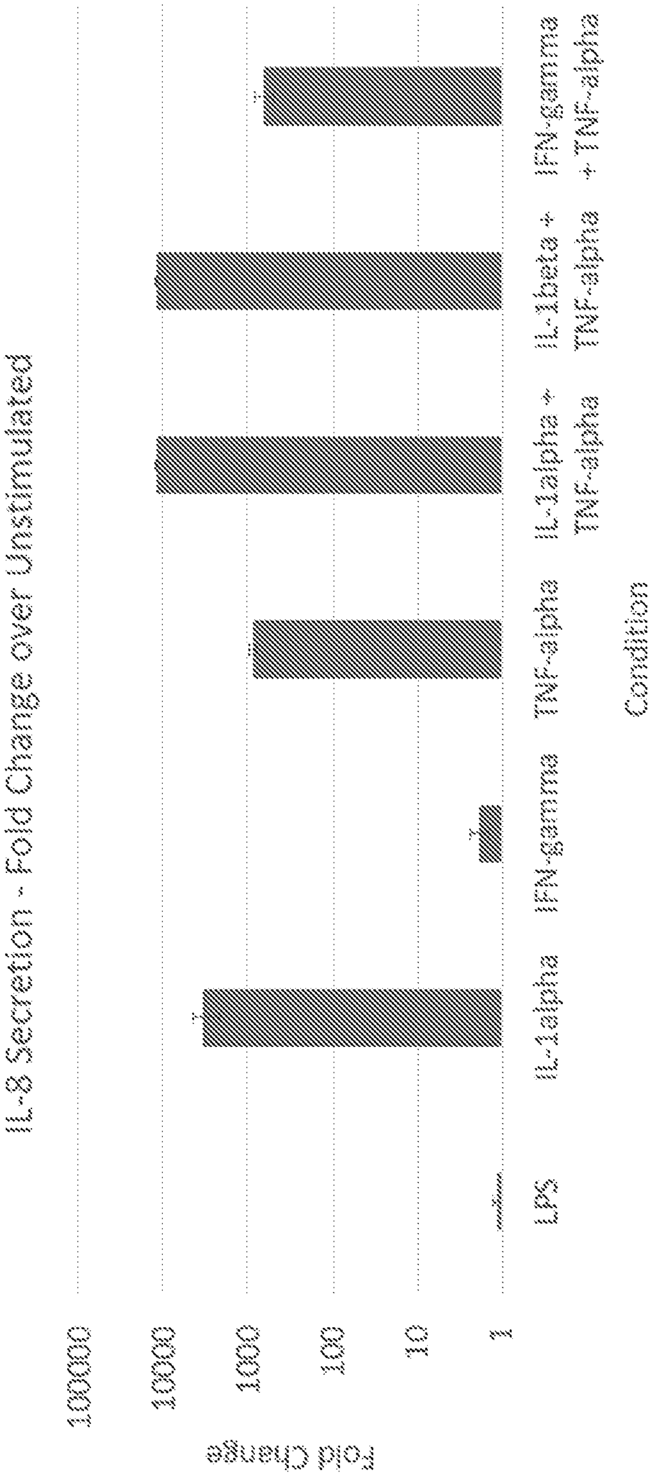

Astrocytes were capable of robust secretion of IL-8/CXCL8 after stimulation with IL-1alpha, TNF-alpha or combinations thereof (FIG. 8C). TNF-alpha alone or combined with IFN-gamma resulted in increased secretion of IL-8 by 898- and 665-fold, respectively, over unstimulated control. IL-alpha stimulation resulted in over 3300-fold increase of IL-8 secretion compared to control. TNF-alpha combined with either IL-1alpha or IL-1beta increased IL-8 secretion by over 12,000-fold compared to control. IL-8/CXCL8 is secreted by astrocytes to attract pro-inflammatory immune cells after insults. This analyte also plays a role in recruitment and differentiation of oligodendrocyte precursor cells (OPCs) to promote remyelination.

Figure 8D:
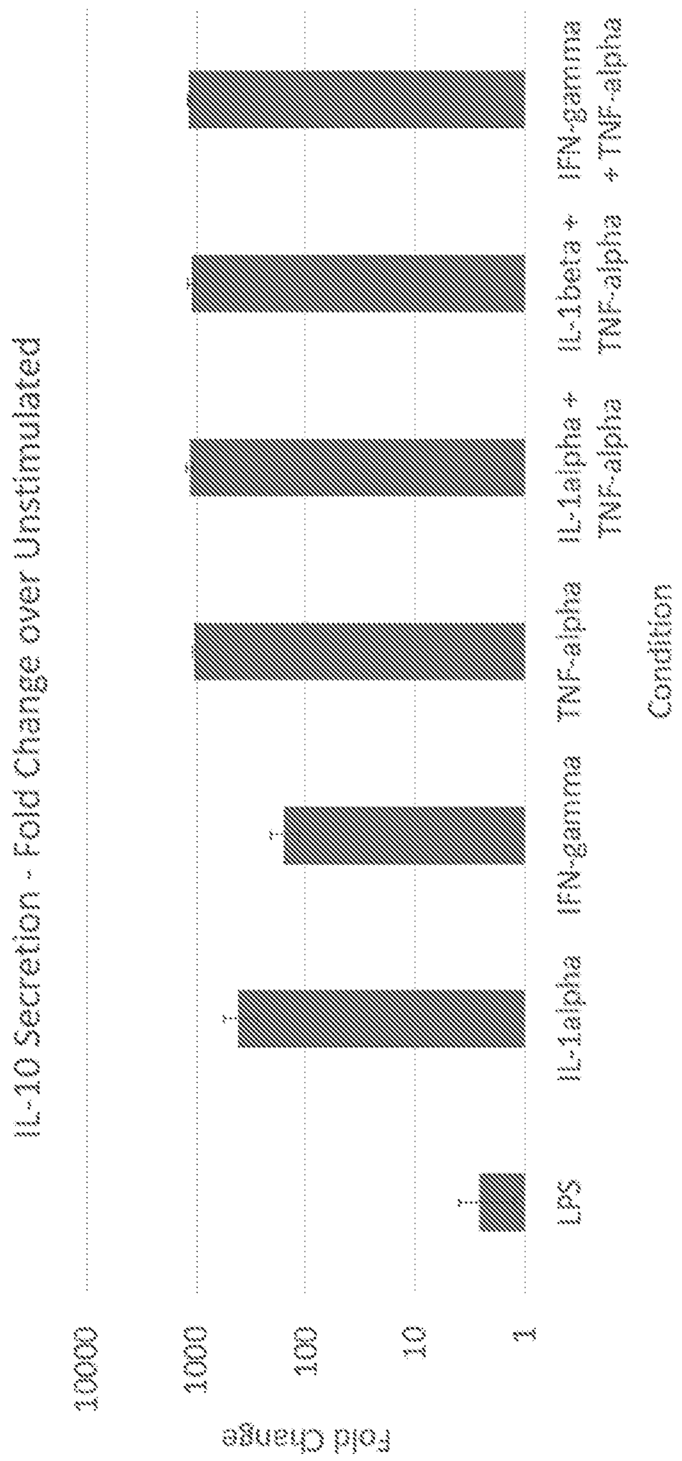

Astrocytes were capable of robust secretion of IL-10 after stimulation with IL-1alpha, IFN-gamma, TNF-alpha or combinations thereof (FIG. 8D). IFN-gamma stimulation resulted in increased secretion of IL-10 by 161-fold over unstimulated control. IL-alpha stimulation resulted in over 415-fold increase of IL-10 secretion compared to control. TNF-alpha alone, or combined with IL-1alpha, IL-1beta or IFN-gamma increased IL-10 secretion by over 1000-fold compared to control. IL-10 is secreted by astrocytes to reduce iNos activity and reduce astrogliosis.

Figure 8E:
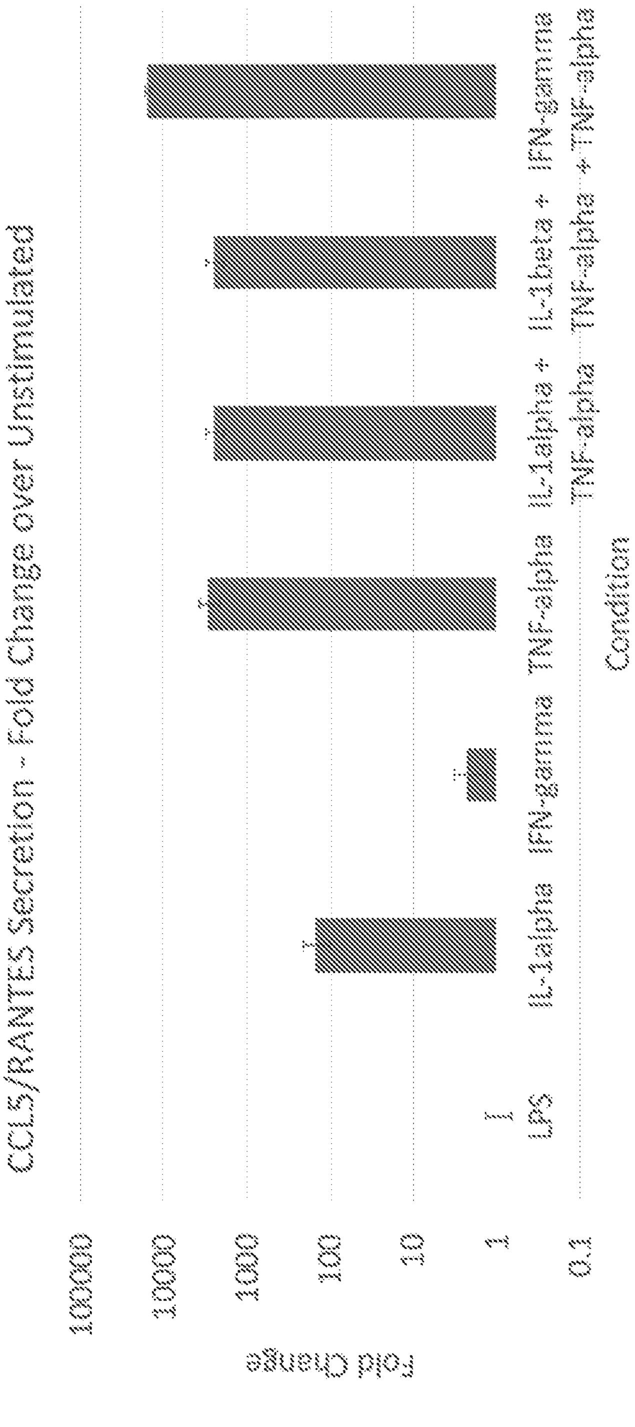

Astrocytes were capable of robust secretion of CCL5/RANTES after stimulation with IL-1alpha, TNF-alpha or combinations thereof (FIG. 8E). IL-1alpha stimulation resulted in increased secretion of CCL5/RANTES by 156-fold over unstimulated control. TNF-alpha alone, or combined with IL-1alpha, IL-1beta or IFN-gamma increased CCL5/RANTES secretion by over 2500-fold compared to control. CCL5/RANTES controls the movements of peripheral immune cells.

Figure 8F:
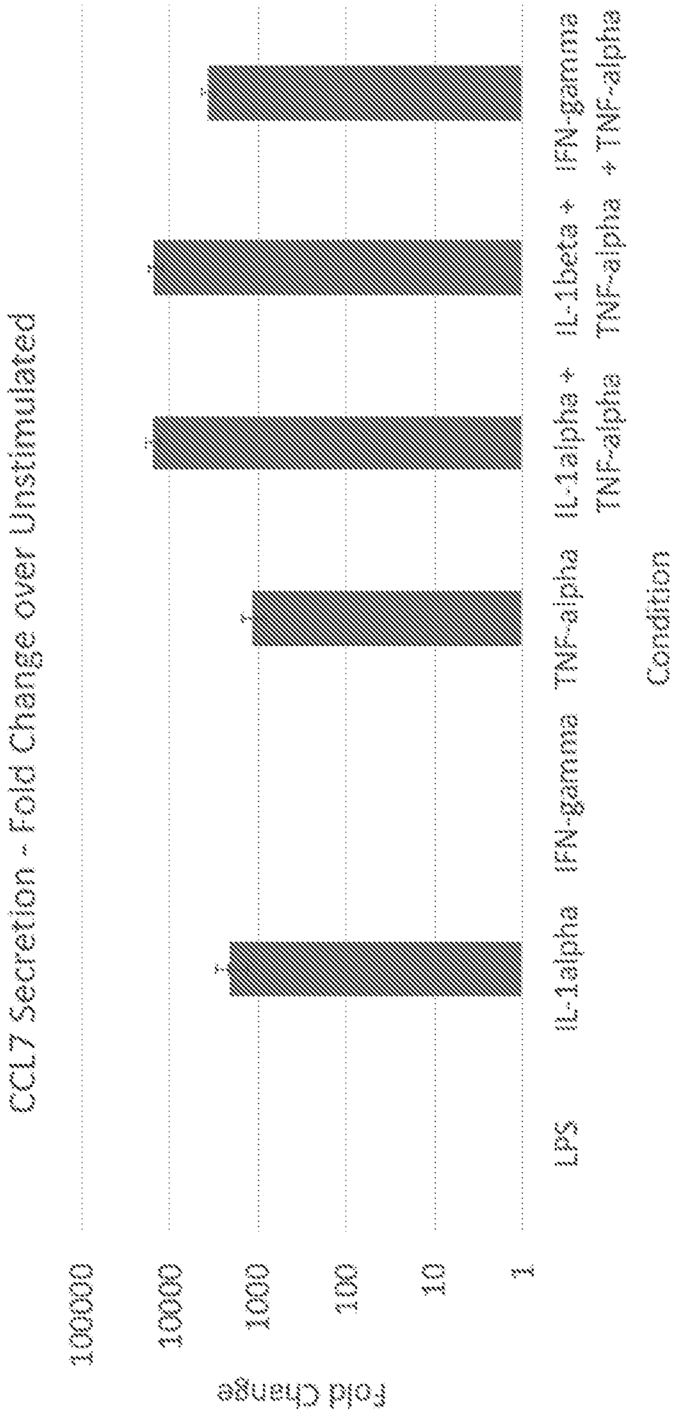

Astrocytes were capable of robust secretion of CCL7 after stimulation with IL-1alpha, TNF-alpha or combinations thereof (FIG. 8F). TNF-alpha stimulation resulted in increased CCL7 secretion of 1184-fold over control. IL-1alpha stimulation resulted in increased secretion of CCL7 by 2177-fold over unstimulated control. IFN-gamma with TNF-alpha stimulation increased CCL7 secretion by 3745-fold over unstimulated control. TNF-alpha combined with IL-1alpha or IL-1beta increased CCL7 secretion by over 15,000-fold compared to control. CCL7 is important for astrocyte-microglia interactions and induces microglia activation.

Figure 8G:
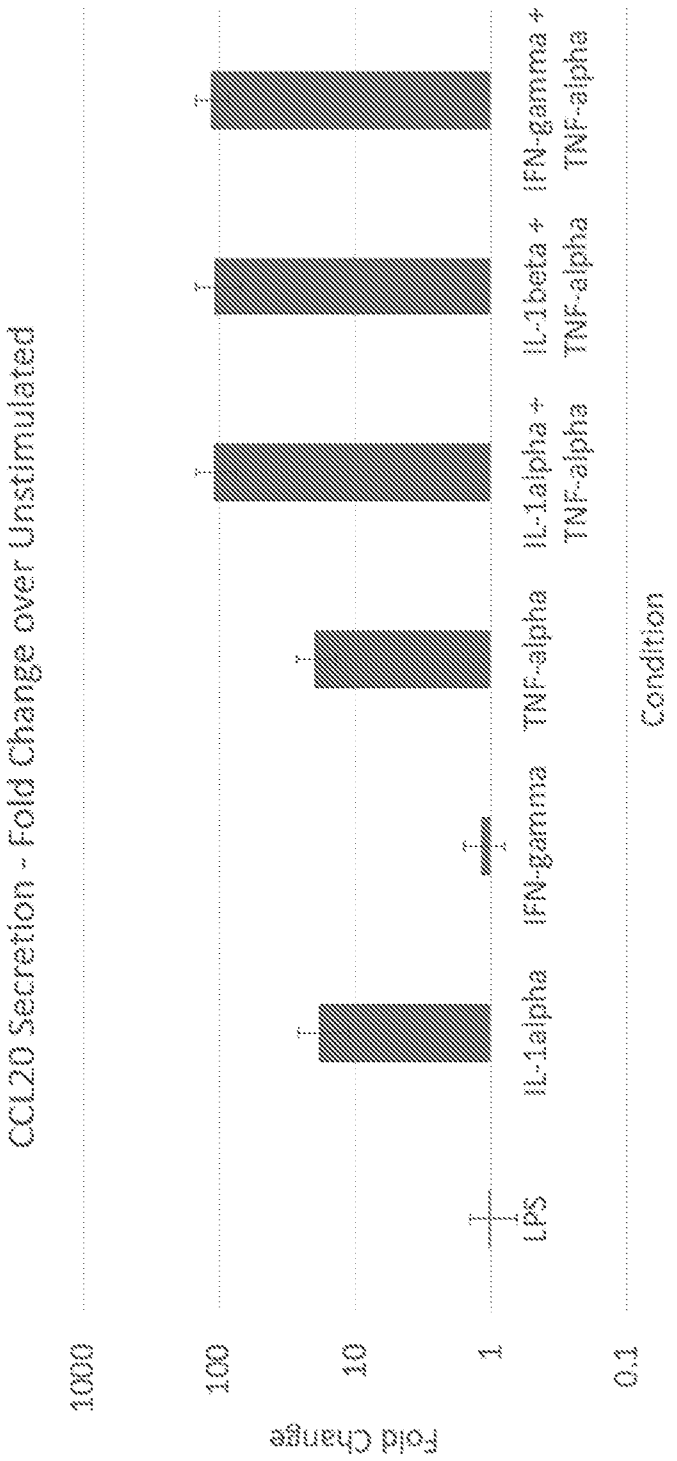

Astrocytes were capable of robust secretion of CCL20 after stimulation with IL-1alpha, TNF-alpha or combinations thereof (FIG. 8G). Stimulation with IL-1alpha or TNF-alpha alone increased CCL20 secretion by over 18-fold over unstimulated control. TNF-alpha combined with IL-1alpha, IL-1beta or IFN-gamma increased CCL20 secretion by over 100-fold compared to control. CCL20 is secreted by astrocytes in response to pro-inflammatory stimuli and attracts T-cells, B-cells and DCs.

Figure 8H:
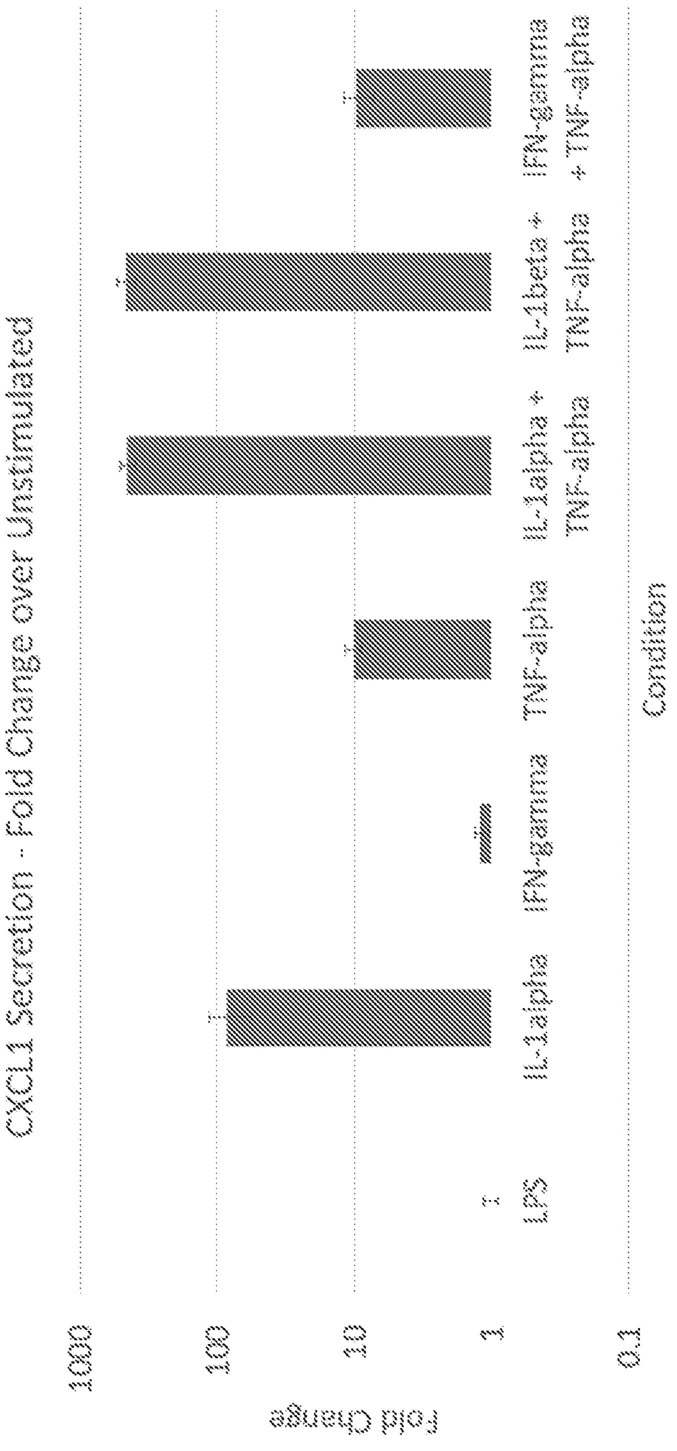

Astrocytes were capable of robust secretion of CXCL1 after stimulation with IL-1alpha, TNF-alpha or combinations thereof (FIG. 8H). TNF-alpha alone or combined with IFN-gamma resulted in over 9-fold secretion of CXCL1 over control. Stimulation with IL-1alpha increased CXCL1 secretion by 84-fold over unstimulated control. TNF-alpha combined with IL-1alpha or IL-1beta increased CXCL1 secretion by over 450-fold compared to control. CXCL1 is secreted by astrocytes to recruit neutrophils to the site of infection, and increases BBB permeability.

Figure 8I:
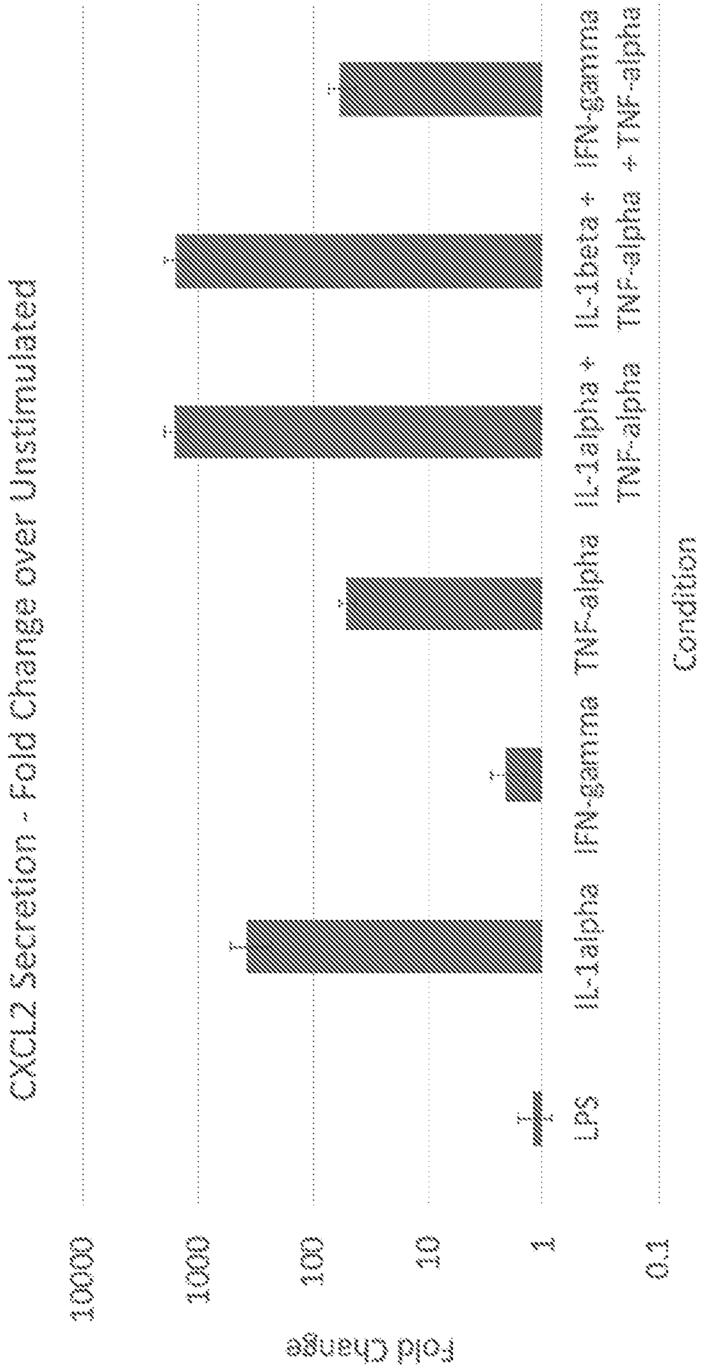

Astrocytes were capable of robust secretion of CXCL2 after stimulation with IL-1alpha, TNF-alpha or combinations thereof (FIG. 8I). TNF-alpha alone or combined with IFN-gamma resulted in over 51-fold secretion of CXCL2 over control. Stimulation with IL-1alpha increased CXCL2 secretion by 379-fold over unstimulated control. TNF-alpha combined with IL-1alpha or IL-1beta increased CXCL2 secretion by over 1585-fold compared to control. CXCL2 activates CXCR2, found on oligodendrocytes and OPCs, which increases OPC proliferation and differentiation.

Figure 8J:
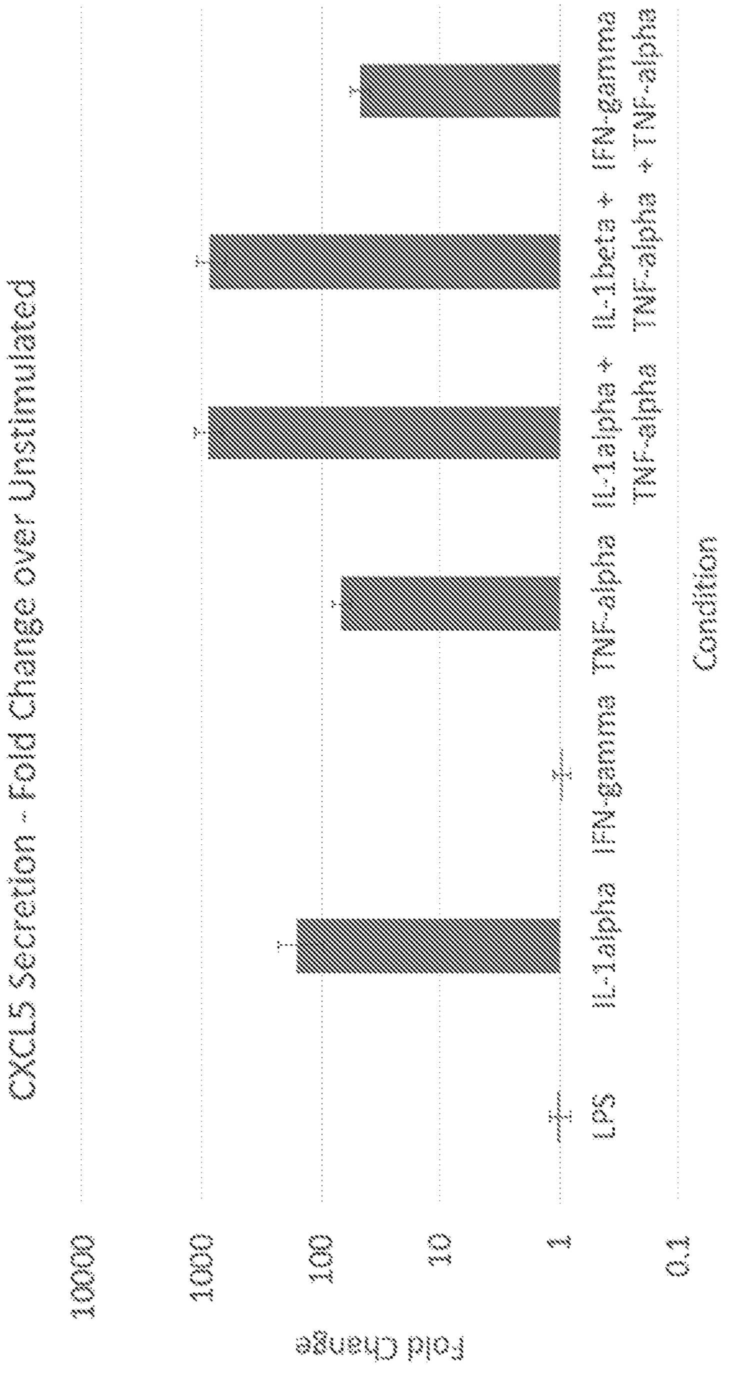

Astrocytes were capable of robust secretion of CXCL5 after stimulation with IL-1alpha, TNF-alpha or combinations thereof (FIG. 8J). TNF-alpha alone or combined with IFN-gamma resulted in over 47-fold secretion of CXCL5 over control. Stimulation with IL-1alpha increased CXCL5 secretion by 161-fold over unstimulated control. TNF-alpha combined with IL-1alpha or IL-1beta increased CXCL5 secretion by over 872-fold compared to control. CXCL5 is secreted by astrocytes in response to injury and activates microglia, resulting in decreased microglia phagocytosis and inhibition.

TABLE 2

| Media compositions. | | | | | | | |
|---|---|---|---|---|---|---|---|
| Media 1 | Media 2 | Media 3 | Media 4 | Media 5 | Media 6 | Media 7 | Media 8 |
| Basal M | Basal M | Basal M | Basal M | Basal M | Basal M | Basal M | Basal M |
| | | | | Lipid Conc. | Lipid Conc. | Lipid Conc. | Lipid Conc. |
| | EGF | CT1 | CT1 EGF | | EGF | CT1 | CT1 EGF |
| Media 9 | Media 10 | Media 11 | Media 12 | Media 13 | Media 14 | Media 15 | Media 16 |
| Basal M JAGG1 | Basal M JAGG1 | Basal M JAGG1 | Basal M JAGG1 | Basal M JAGG1 | Basal M JAGG1 | Basal M JAGG1 | Basal M JAGG1 |
| | | | | Lipid Conc. | Lipid Conc. | Lipid Conc. | Lipid Conc. |
| | EGF | CT1 | CT1 EGF | | EGF | CT1 | CT1 EGF |
| Media 17 | Media 18 | Media 19 | Media 20 | Media 21 | Media 22 | Media 23 | Media 24 |
| Basal M DLL1 | Basal M DLL1 | Basal M DLL1 | Basal M DLL1 | Basal M DLL1 | Basal M DLL1 | Basal M DLL1 | Basal M DLL1 |

TABLE 2-continued

Media compositions.

| | | | | | | |
|---|---|---|---|---|---|---|
| | | | Lipid Conc. | Lipid Conc. | Lipid Conc. | Lipid Conc. |
| EGF | CT1 | CT1<br>EGF | | EGF | CT1 | CT1<br>EGF |
| Media 25 | Media 26 | Media 27 | Media 28 | Media 29 | Media 30 | Media 31 |
| Basal M<br>DLL1<br>JAGG1 | Basal M<br>DLL1<br>JAGG1 | Basal M<br>DLL1<br>JAGG1 | Basal M<br>DLL1<br>JAGG1 | Basal M<br>DLL1<br>JAGG1 | Basal M<br>DLL1<br>JAGG1 | Basal M<br>DLL1<br>JAGG1 |
| | | | | Lipid Conc. | Lipid Conc. | Lipid Conc. |
| | EGF | CT1 | CT1<br>EGF | EGF | CT1 | CT1<br>EGF |

| Basal Medium | Final Concentration |
|---|---|
| DMEM/F12 | |
| N2 | 1% |
| B27 + RA | 2% |
| GlutaMAX | 1% |
| Pen/Strep | 1% |
| OSM | 10 ng/mL |
| CNTF | 10 ng/mL |
| LIF | 10 ng/mL |

| Variable components | Final Concentration |
|---|---|
| DLL1 | 10 ng/mL |
| JAGG1 | 10 ng/mL |
| Lipid Concentrate | 2% |
| CT-1 | 10 ng/mL |
| EGF | 20 ng/mL |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alexander et al., *Proc. Nat. Acad. Sci. USA,* 85:5092-5096, 1988.

Ausubel et al., *Current Protocols in Molecular Biology*, Greene Publ. Assoc. Inc. & John Wiley & Sons, Inc., MA, 1996. Blomer et al., 1997

Chen et al., *Nature Methods* 8:424-429, 2011.

Ercolani et al., *J. Biol. Chem.,* 263:15335-15341, 1988.

Evans, et al., In: Cancer *Principles and Practice of Oncology*, Devita et al. (Eds.), Lippincot-Raven, NY, 1054-1087, 1997. Fechheimer et al., *Proc Natl. Acad. Sci. USA,* 84:8463-8467, 1987.

International Publication No. WO 2012/149484

International Publication No. WO 02/016536

International Publication No. WO 03/016496

International Publication No. WO 2007/069666

International Publication No. WO 2007/069666

International Publication No. WO 98/30679

International Publication No. WO 98/30679

International Publication No. WO 98/53058

International Publication No. WO 98/53059

International Publication No. WO 98/53060

Karin et al. *Cell,* 36:371-379, 1989.

Langle-Rouault et al., *J. Virol.,* 72(7):6181-6185, 1998.

Levitskaya et al., *Proc. Natl. Acad. Sci. USA,* 94(23):12616-12621, 1997.

Ludwig et al., *Nat. Biotechnol.,* 24:185-187, 2006b.

Ludwig et al., *Nat. Methods,* 3:637-646, 2006a.

Maniatis, et al., *Molecular Cloning, A Laboratory Manual*, Cold Spring Harbor Press, Cold Spring Harbor, N.Y., 1988.

Ng, *Nuc. Acid Res.,* 17:601-615, 1989.

Pelletier and Sonenberg, *Nature,* 334(6180):320-325, 1988.

Quitsche et al., *J. Biol. Chem.,* 264:9539-9545, 1989.

Richards et al., *Cell,* 37:263-272, 1984.

Sambrook and Russell, *Molecular Cloning: A Laboratory Manual,* 3rd Ed. Cold Spring Harbor 1997.

Takahashi et al., *Cell,* 131:861-872, 2007.

U.S. Pat. No. 4,683,202
U.S. Pat. No. 5,556,954
U.S. Pat. No. 5,925,565
U.S. Pat. No. 5,928,906
U.S. Pat. No. 5,935,819
U.S. Pat. No. 6,103,470
U.S. Pat. No. 6,140,081
U.S. Pat. No. 6,416,998
U.S. Pat. No. 6,453,242
U.S. Pat. No. 6,534,261
U.S. Pat. No. 7,442,548
U.S. Pat. No. 7,598,364
U.S. Pat. No. 7,682,828
U.S. Pat. No. 7,989,425
U.S. Pat. No. 8,058,065
U.S. Pat. No. 8,071,369
U.S. Pat. No. 8,129,187
U.S. Pat. No. 8,268,620
U.S. Pat. No. 8,278,620
U.S. Pat. No. 8,546,140
U.S. Pat. No. 8,546,140
U.S. Pat. No. 8,741,648
U.S. Patent Publication No. 2002/0076747
U.S. Patent Publication No. 2002/0076747
U.S. Patent Publication No. 20020055144
U.S. Patent Publication No. 2003/0211603
U.S. Patent Publication No. 2005/0064474
U.S. Patent Publication No. 2005/0260186
U.S. Patent Publication No. 2006/0104968
U.S. Patent Publication No. 2006/0188987
U.S. Patent Publication No. 2007/0218528
U.S. Patent Publication No. 20090148425
U.S. Patent Publication No. 20090246875
U.S. Patent Publication No. 2010/0210014
U.S. Patent Publication No. 2011/0301073
U.S. Patent Publication No. 2011/0301073
U.S. Patent Publication No. 2011/0301073
U.S. Patent Publication No. 2012/0196360
U.S. Patent Publication No. 20120276636
Yamanaka et al., *Cell,* 131(5):861-72, 2007.
Yu et al., *Science,* 318:1917, 2007.

What is claimed is:

1. An in vitro method for producing astrocytes from induced pluripotent stem cells (iPSCs) comprising:

(a) obtaining a starting population of neural precursor cells (NPCs) derived from iPSCs;

(b) culturing the NPCs in the presence of leukemia inhibitory factor protein (LIF), Ciliary-Derived Neurotrophic Factor protein (CNTF), oncostatin-M protein (OSM), Jagged 1 Fc chimera protein (JAGG1), and EGF for a period of time sufficient to produce astrocyte progenitor cells (APCs); and (c) further culturing the APCs in the presence of LIF, CNTF and a lipid concentrate comprising arachidonic acid, cholesterol, DL-alpha-Tocopherol Acetate, linoleic acid, linolenic acid, myristic acid, oleic acid, palmitic acid, palmitoleic acid, and/or stearic acid for a period of time sufficient to produce a population of astrocytes.

2. The method of claim 1, wherein obtaining the starting population of NPCs comprises:

(a) culturing iPSCs on an extracellular matrix (ECM) protein coated surface in the presence of a ROCK inhibitor;

(b) further culturing the iPSCs in the absence of a ROCK inhibitor or blebbistatin;

(c) pre-conditioning the iPSCs in the presence of a GSK3 inhibitor;

(d) differentiating the iPSCs to a population of NPCs.

3. The method of claim 2, wherein the ECM protein is laminin, fibronectin, vitronectin, basement membrane extract (BME) purified from murine Engelbreth-Holm-Swarm tumor, tenascin, entactin, thrombospondin, elastin, gelatin, and/or collagen.

4. The method of claim 2, wherein the method comprises culturing in the absence of SMAD inhibitors.

5. The method of claim 2, wherein the GSK3 inhibitor is CHIR99021, BIO, or SB-216763.

6. The method of claim 2, wherein the population of NPCs are at least 70% percent positive for CD24 and Nestin.

7. The method of claim 2, wherein the APCs have decreased expression of SSEA-4 and TRA-1-60 as compared to the iPSCs after step (b).

8. The method of claim 1, wherein the iPSCs are derived from a donor with Alexander's disease or leukodystrophy.

9. The method of claim 1, wherein the iPSCs comprise a disruption in TREM2, APOE, Methyl-CpG Binding Protein 2 (MeCP2), and/or Alpha-synuclein (SCNA).

10. The method of claim 1, wherein the astrocytes are end stage astrocytes positive for CD44, S100b, NFIX, GLAST, and/or GFAP.

11. The method of claim 10, wherein the astrocytes have functional glutamate uptake and/or development of a neural network.

12. The method claim 1, wherein step (b) further comprises culturing in the presence of lipid concentrate, EGF, JAGG1, and/or DLL1.

13. The method of claim 1, wherein step (b) comprises culturing in the further presence of lipid concentrate.

14. The method of claim 1, wherein step (b) comprises culturing in the further presence of DLL1 and lipid concentrate.

15. The method of claim 1, wherein the APCs are cultured in the further presence of oncostatin-M, and/or CT-1.

16. The method of claim 1, wherein the population of astrocytes is at least 80% positive for S100B, CD44, and/or NFIX and/or at least 30% positive for CD56 and/or GFAP.

17. The method of claim 1, wherein the astrocytes secrete IL-1ra, IL-6, IL-8 (CXCL8), IL-10, CCL5 (RANTES), CCL7, CCL20, CXCL1, CXCL2 and/or CXCL5 after stimulation with IL-1$\alpha$ and/or TNF$\alpha$.

18. The method of claim 1, wherein the lipid concentrate comprises arachidonic acid, cholesterol, DL-alpha-Tocopherol Acetate, linoleic acid, linolenic acid, myristic acid, oleic acid, palmitic acid, palmitoleic acid, and stearic acid.

19. The method of claim 1, wherein the lipid concentrate is present at a concentration of 1% to 5%.

20. A pharmaceutical composition comprising an astrocyte cell population produced according to claim 1, a cryoprotectant, and a pharmaceutically acceptable carrier, wherein the astrocyte cell population is at least 70% positive for NFIX and CD56.

21. The composition of claim 20, wherein the cryoprotectant is serum albumin or dimethylsulfoxide (DMSO).

* * * * *